US009522280B2

(12) United States Patent
Fishler et al.

(10) Patent No.: US 9,522,280 B2
(45) Date of Patent: Dec. 20, 2016

(54) LEADLESS DUAL-CHAMBER PACING SYSTEM AND METHOD

(71) Applicant: Pacesetter, Inc., Sunnyvale, CA (US)

(72) Inventors: Matthew G. Fishler, Santa Cruz, CA (US); Benjamin T. Persson, Sunnyvale, CA (US); Suresh Gurunathan, Palo Alto, CA (US); Donald Chin, Palo Alto, CA (US); Stephen J. Swift, San Diego, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/931,698

(22) Filed: Nov. 3, 2015

(65) Prior Publication Data

US 2016/0121128 A1    May 5, 2016

Related U.S. Application Data

(60) Provisional application No. 62/084,476, filed on Nov. 25, 2014, provisional application No. 62/074,541, filed on Nov. 3, 2014.

(51) Int. Cl.

| A61N 1/372 | (2006.01) |
|---|---|
| A61N 1/365 | (2006.01) |
| A61N 1/375 | (2006.01) |
| A61N 1/362 | (2006.01) |
| H04W 52/04 | (2009.01) |
| H04W 56/00 | (2009.01) |
| A61N 1/37 | (2006.01) |

(52) U.S. Cl.
CPC ......... *A61N 1/37288* (2013.01); *A61N 1/3622* (2013.01); *A61N 1/3756* (2013.01); *A61N 1/37235* (2013.01); *H04W 52/04* (2013.01); *H04W 56/001* (2013.01); *A61N 1/36514* (2013.01); *A61N 1/3702* (2013.01); *A61N 1/37217* (2013.01)

(58) Field of Classification Search
None
See application file for complete search history.

(56) References Cited

U.S. PATENT DOCUMENTS 8,457,742 B2 *   6/2013   Jacobson ............. A61N 1/3621
                                                              607/2

* cited by examiner

*Primary Examiner* — Brian T Gedeon
(74) *Attorney, Agent, or Firm* — Theresa A. Raymer

(57) ABSTRACT

In accordance with an embodiment, a system and method is provided for providing communications between first and second implantable medical devices (IMDs). The system comprises a first implantable medical device (IMD) configured to transmit a first event message during or preceding a first cardiac cycle, and a second IMD configured to receive the first event message, wherein receipt of the first event message configures the second IMD to generate pacing pulses for only a predetermined number ("n") of consecutive cardiac cycles, wherein n is an integer equal to or greater than 2. The method comprises transmitting a first event message during or preceding a first cardiac cycle from the first IMD, receiving the first event message at the second IMD, in response to receiving the first event message, arming the second IMD to generate a pacing pulse for a second cardiac cycle, and arming the second IMD to generate a pacing pulse for only a predetermined number of consecutive cardiac cycles immediately subsequent to the second cardiac cycle.

16 Claims, 19 Drawing Sheets

LEADLESS DUAL-CHAMBER PACING SYSTEM AND METHOD

CROSS REFERENCE TO RELATED APPLICATIONS

This application claims the benefit of U.S. Provisional Application No. 62/084,476, entitled IMPLANTABLE DEVICE INTRA-CARDIAC COMMUNICATIONS SYSTEM AND METHOD, filed Nov. 25, 2014. This application also claims the benefit of U.S. Provisional Application No. 62/074,541, entitled IMPLANTABLE DEVICE INTRA-CARDIAC COMMUNICATIONS SYSTEM AND METHOD, filed Nov. 3, 2014. Each patent application identified above is incorporated herein by reference in its entirety to provide continuity of disclosure.

FIELD OF THE INVENTION

Embodiments herein generally relate to methods and systems for communication between implantable devices.

BACKGROUND OF THE INVENTION

Currently, implantable medical devices (IMDs) utilize one or more electrically-conductive leads (which traverse blood vessels and heart chambers) in order to connect a canister with electronics and a power source (the can) to electrodes affixed to the heart for the purpose of electrically exciting cardiac tissue (pacing) and measuring myocardial electrical activity (sensing). These leads may experience certain limitations, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction. Further, conventional pacemakers with left ventricle (LV) pacing/sensing capability require multiple leads and a complex header on the pacemaker.

A small sized IMD has been proposed that mitigates the aforementioned complications, termed a leadless pacemaker (LP) that is characterized by the following features: electrodes are affixed directly to the "can" of the device; the entire device is attached to or within the heart; and the LP is capable of pacing and sensing in the chamber of the heart where it is implanted.

The LPs that have been proposed thus far offer limited functional capability. The LP is able to sense in one chamber and deliver pacing pulses in that same chamber, and thus offer single chamber functionality. For example, an LP device that is located in the right atrium would be limited to offering AAI mode functionality. An AAI mode LP can only sense in the right atrium, pace in the right atrium and inhibit pacing function when an intrinsic event is detected in the right atrium within a preset time limit. Similarly, an LP device that is located in the right ventricle would be limited to offering VVI mode functionality. A VVI mode LP can only sense in the right ventricle, pace in the right ventricle and inhibit pacing function when an intrinsic event is detected in the right ventricle within a preset time limit.

It has been proposed to implant sets of multiple LP devices within a single patient, such as one or more LP devices located in the right atrium and one or more LP devices located in the right ventricle. The atrial LP devices and the ventricular LP devices wirelessly communicate with one another to convey pacing and sensing information there between to coordinate pacing and sensing operations between the various LP devices.

A master/slave relationship may be used to coordinate pacing and sensing operations between the multiple LP devices. A strict master/slave configuration, however, requires that, for example, an "atrial pace" ("AP") command be transmitted from the master ventricle LP to the slave atrial LP at a time when the ventricle may be in a vulnerable period. These AP commands could in theory have a risk of inducing premature ventricular excitations, which under worst-case consideration, could degenerate into sustained ventricular tachycardia or ventricular fibrillation, which may be lethal to the patient.

SUMMARY

In accordance with an embodiment, a system is provided for providing communications between first and second implantable medical devices (IMDs). The system comprises a first implantable medical device (IMD) configured to transmit a first event message during or preceding a first cardiac cycle, and a second IMD configured to receive the first event message, wherein receipt of the first event message configures the second IMD to generate pacing pulses for only a predetermined number ("n") of consecutive cardiac cycles, wherein n is an integer equal to or greater than 2.

In accordance with an embodiment, a method is provided for providing communications between first and second implantable medical devices (IMDs). The method comprises transmitting a first event message during or preceding a first cardiac cycle from the first IMD, receiving the first event message at the second IMD, in response to receiving the first event message, arming the second IMD to generate a pacing pulse for a second cardiac cycle, and arming the second IMD to generate a pacing pulse for only a predetermined number of consecutive cardiac cycles immediately subsequent to the second cardiac cycle.

In another embodiment, the present disclosure is directed to a system for applying cardiac stimulation to a patient. The system includes a first leadless pacemaker (LP) implanted in a first chamber of a heart of the patient, and a second LP implanted in a second chamber of the heart of the patient, wherein the second LP is configured to receive an event message that includes an arm command from the first LP, in response to receiving the event message, arm by initiating a first timer having a first interval escape duration, and deliver a first pace pulse when the timer expires.

In another embodiment, the present disclosure is directed to a leadless pacemaker (LP) for use in a cardiac stimulation system, the LP configured to be implanted in a chamber of a heart of a patient. The LP includes a memory, and a processor coupled to the memory, the processor configured to receive an arm command included in an event message from a remote LP that is implanted in a different chamber than the first LP, in response to receiving the arm command, arm the LP by initiating a first timer having a first event to event duration, and cause the LP to deliver a first pace pulse when the timer expires.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

In some embodiments of an illustrative cardiac pacing system, pacing and sensing operations of multiple medical devices, which may include one or more leadless cardiac pacemakers, an ICD, such as a subcutaneous-ICD, and/or a programmer reliably and safely coordinate pacing and/or sensing operations.

Figure 1:
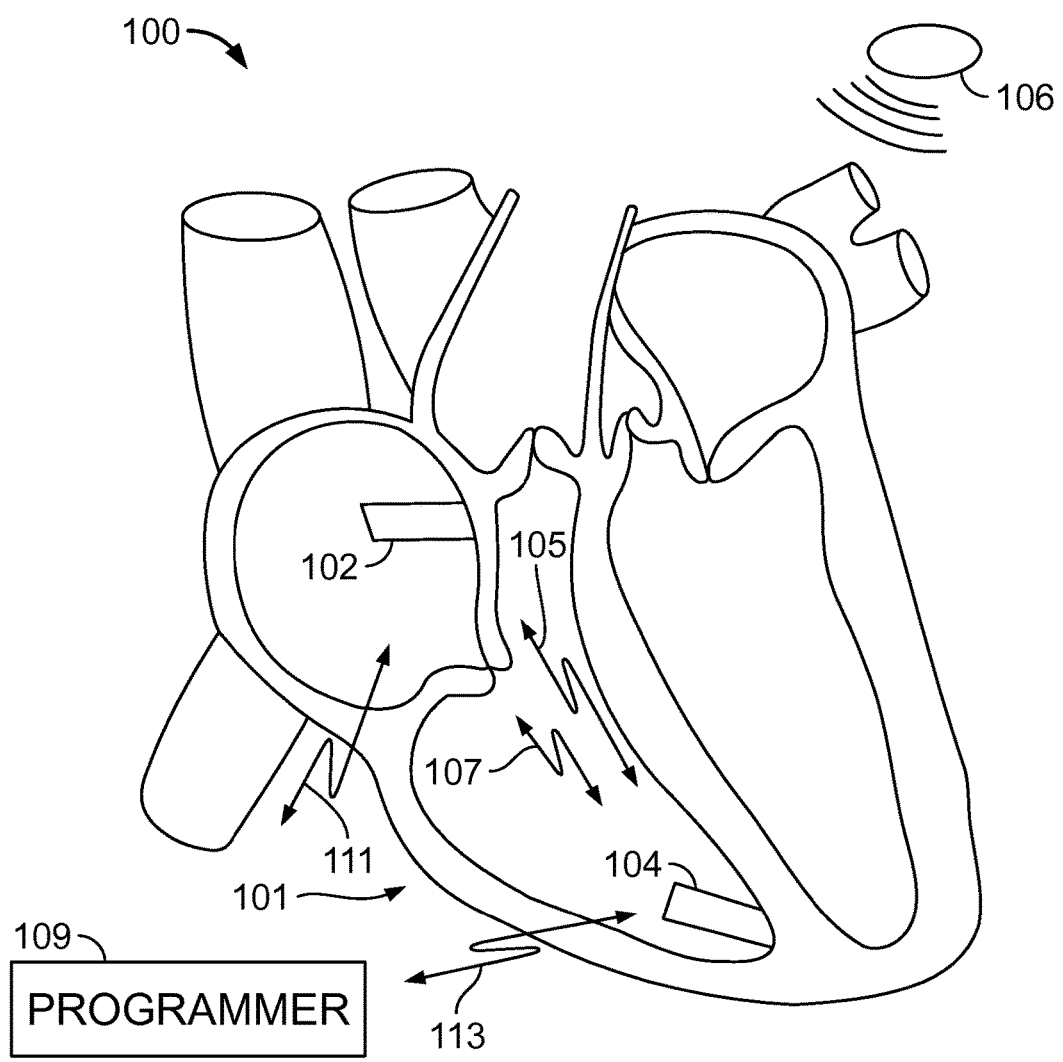
FIG. 1 illustrates a system formed in accordance with embodiments herein as implanted in a heart.

FIG. 1 illustrates a system 100 formed in accordance with embodiments herein as implanted in a heart 101. The system 100 comprises two or more leadless pacemakers (LPs) 102 and 104 located in different chambers of the heart. LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In some embodiments, LPs 102 and 104 communicate with one another, with an ICD 106, and with an external device (programmer) 109 through wireless transceivers, communications coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more leadless cardiac pacemakers 102 and 104 can be co-implanted with the implantable cardioverter-defibrillator (ICD) 106. Each leadless cardiac pacemaker 102, 104 uses two or more electrodes located within, on, or within a few centimeters of the housing of the pacemaker, for pacing and sensing at the cardiac chamber, for bidirectional communication with one another, with the programmer 109, and the ICD 106.

In accordance with one embodiment, a method is provided for coordinating operation between leadless pacemakers (LPs) located in different chambers of the heart. The method configures a local LP to receive communications from a remote LP through conductive communication.

While the methods and systems described herein include examples primarily in the context of LPs, it is understood that the methods and systems herein may be utilized with various other external and implanted devices. By way of example, the methods and systems may coordinate operation between various implantable medical devices (IMDs) implanted in a human, not just LPs. The methods and systems comprise configuring a first IMD to receive communications from at least a second IMD through conductive communication over at least a first channel. It should also be understood that the methods and systems may coordinate operation between multiple IMDs, and are not limited to coordinate operation between just a first and second IMD. The methods and systems may also be used to coordinate operation of two or more IMDs implanted within the same chamber that may be the same type of IMD or may be different types of IMDs. The methods and systems may also be used to coordinate operation of two or more IMDs in a system comprising at least one IMD implanted but not within a heart chamber, e.g., epicardially, transmurally, intravascularly (eg, coronary sinus), subcutaneously (e.g., S-ICD), etc.

Figure 2:
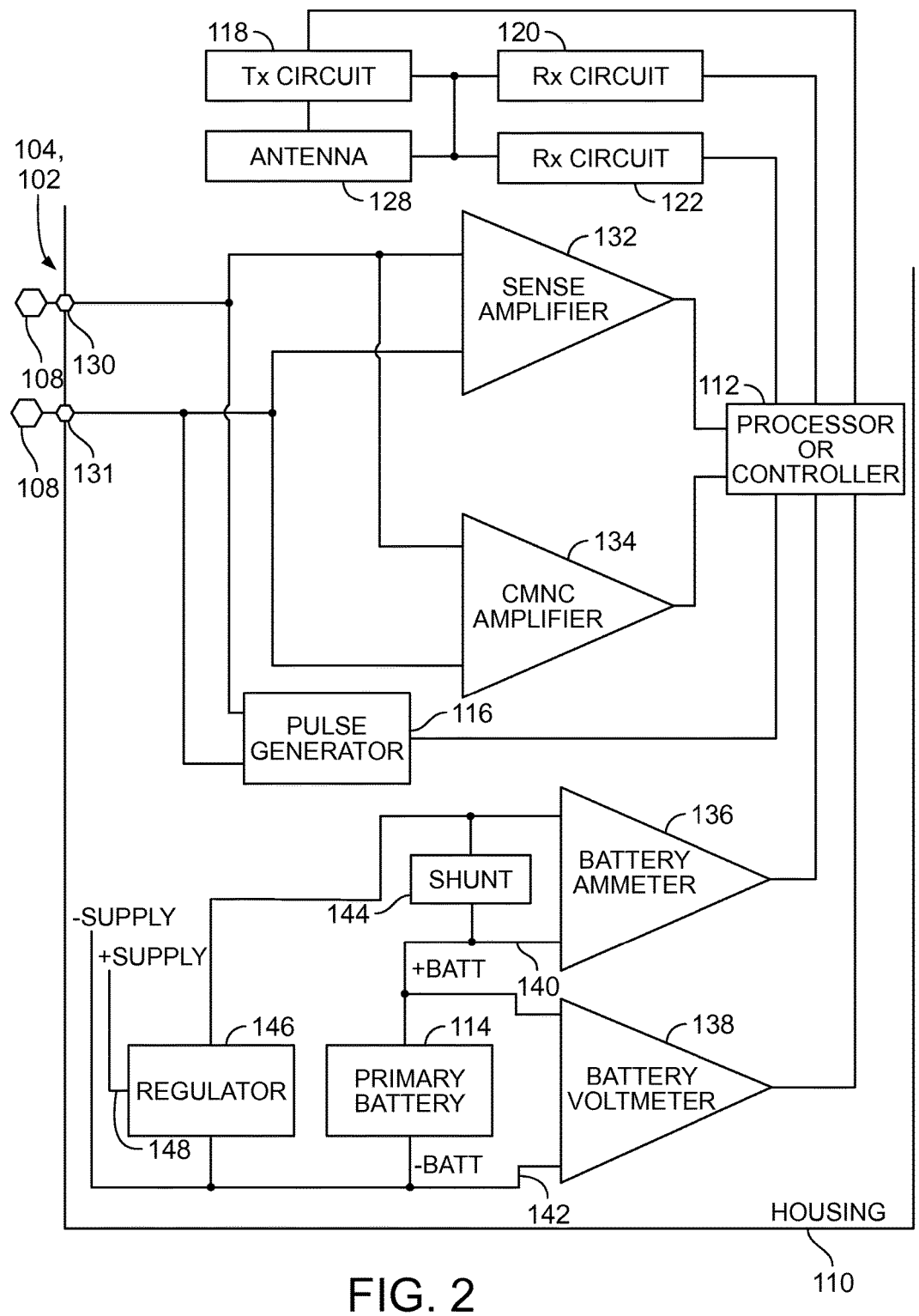
FIG. 2 is a block diagram of a single LP in accordance with embodiments herein.

Referring to FIG. 2, a pictorial diagram shows an embodiment for portions of the electronics within LP 102, 104 configured to provide conducted communication through the sensing/pacing electrode. One or more of LPs 102 and 104 comprise at least two leadless electrodes 108 configured for delivering cardiac pacing pulses, sensing evoked and/or natural cardiac electrical signals, and uni-directional or bi-directional communication.

LP 102, 104 includes a transmitter 118 and first and second receivers 120 and 122 that collectively define separate first and second communications channels 105 and 107 (FIG. 1), (among other things) between LPs 102 and 104. Although first and second receivers 120 and 122 are depicted, in other embodiments, LP 102, 104 may only include first receiver 120, or may include additional receivers other than first and second receivers 120 and 122. LP 102, 104 may only also include one or more transmitters in addition to transmitter 118. In certain embodiments, LPs 102 and 104 may communicate over more than just first and second communications channels 105 and 107. In certain embodiments, LPs 102 and 104 may communicate over one common communication channel 105. The transmitter 118 and receiver(s) 120, 122 may each utilize a separate antenna or may utilize a common antenna 128. Optionally, LPs 102 and 104 communicate conductively over a common physical channel via the same electrodes 108 that are also used to deliver pacing pulses. Usage of the electrodes 108 for communication enables the one or more leadless cardiac pacemakers 102 and 104 for antenna-less and telemetry coil-less communication.

When LP 102, 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wake up notice) followed by an event marker. The notice trigger pulse is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or IMD) that receives any implant to implant (i2i) communication from another LP (or IMD) or from an external device may transmit a receive acknowledgement indicating that the receiving LP/IMD received the i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Embodiments herein describe efficient and reliable processes to maintain synchronization between LPs 102 and 104 without maintaining continuous communication between LPs 102 and 104. In accordance with embodiments herein, the transmitter(s) 118 and receiver(s) 120, 122 utilize low power event messages/signaling between multiple LPs 102 and 104. The low power event messages/signaling may be maintained between LPs 102 and 104 synchronously or asynchronously.

For synchronous event signaling, LPs 102 and 104 maintain synchronization and regularly communicate at a specific interval. Synchronous event signaling allows the transmitter and receivers in each LP 102,104 to use limited (or minimal) power as each LP 102, 104 is only powered for a small fraction of the time in connection with transmission and reception. For example, LP 102, 104 may transmit/receive (Tx/Rx) communications in time slots having duration of 10-20 µs, where the Tx/Rx time slots occur periodically (e.g., every 10-20 ms). In the foregoing example, a receiver 120, 122 that is active/ON for select receive time slots, that are spaced apart several milliseconds, may draw an amount of current that is several times less (e.g., 1000× less) than a current draw of a receiver that is "always on."

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. During asynchronous event signaling, one or more of receivers 120 and 122 of LPs 102 and 104 are "always on" to search for incoming transmissions. However, maintaining LP receiver 120, 122 in an "always on" state presents challenges as the received signal level often is low due to high channel attenuation caused by the patient's anatomy.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of $\frac{1}{500}$ to $\frac{1}{10000}$. A gain factor may be $\frac{1}{1000}$th. Transmit current is a design factor in addition to receiver current. As an example, the system may allocate one-half of the implant communication current budget to the transmitter (e.g., 0.5 µA for each transmitter). When LP 102, 104 maintains a transmitter in a continuous on-state and the electrode load is 500 ohms, a transmitted voltage may be 0.250 mV. When an event signal is transmitted at 0.250 mV, the event signal is attenuated as it propagates and would appear at LP 102, 104 receiver as an amplitude of approximately 0.25 µV. The receivers 120 and 122 utilize a synchronization threshold to differentiate incoming communications signals from noise. As an example, the synchronization threshold may be 0.5 µV (or more generally 0.25 µV to 5 µV), which would cause LP 102, 104 receiver to reject an incoming communications signal that exhibits a receive voltage below 0.5 µV.

To overcome the foregoing receive power limit, a pulsed transmission scheme may be utilized in which communications transmissions occur correlated with an event. By way of example, the pulsed transmission scheme may be simplified such that each transmission constitutes a single pulse of a select amplitude and width.

When LP transmitter 118 transmits event signals over a conductive communication channel that has an electrode load of 500 ohm using a 1 ms pulse width at 2.5V at a rate of 60 bpm, LP transmitter 118 will draw 4.4 µA for transmit current. When LP transmitter 118 transmits event signals at 2.5V using a 2 µs pulse width, transmitter 118 only draws 10 nA to transmit event messages at a rate of 60 bpm. In order to sense an event message (transmitted with the foregoing parameters), receivers 120 and 122 may utilize 50 µA. In accordance with embodiments herein, the pulse widths and other transmit/receive parameters may be adjusted to achieve a desired total (summed) current demand from both transmitter 118 and receivers 120 and 122. The transmitter current decreases nearly linearly with narrowing bandwidth (pulse width), while a relation between receiver current and bandwidth is non-linear.

In accordance with embodiments herein, LPs 102 and 104 may utilize multi-stage receivers that implement a staged receiver wakeup scheme in order to improve reliability yet remain power efficient. Each of LPs 102 and 104 may include first and second receivers 120 and 122 that operate with different first and second activation protocols and different first and second receive channels. For example, first receiver 120 may be assigned a first activation protocol that is "always on" and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/less than 10 µs per pulse) assigned to the second receive channel. First receiver 120 may maintain the first channel active for at least a portion of a time when the second channel is inactive to listen for event messages from a remote LP. The controller or processor determines whether the incoming signal received over the first channel corresponds to an LP wakeup notice. The second receiver 122 may be assigned a second activation protocol that is a triggered protocol, in which the second receiver 122 becomes active in response to detection of trigger events over the first receive channel (e.g., when the incoming signal corresponds to the LP wakeup notice, activating the second channel at the local LP). Further examples in accordance with the present disclosure of a staged receiver wakeup scheme are disclosed in U.S. Provisional Application Nos. 62/084,476 and 62/074,541.

The marker message may represent a signature indicative of an event qualification to qualify a valid event marker pulse. The event qualification messages distinguish a message from spurious noise and avoid mistaking other signals as event messages having implant markers. The event message may be repeated to allow the LP receiver 120 multiple chances to "catch" the event qualification. Additionally or alternatively, the Tx and Rx LP 102, 104 may implement a handshaking protocol in which the Tx and Rx LP 102, 104 exchange additional information, such as to allow a response to follow the marker. The exchange of additional information may be limited or avoided in certain instances as the exchange draws additional power when sending and receiving the information. Optionally, the event message may be configured with additional content to provide a more robust event marker.

Transmitter 118 may be configured to transmit the event messages in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with embodiments herein, programmer 109 may communicate over a programmer-to-LP channel, with LP 102, 104 utilizing the same communication scheme. The external programmer may listen to the event message transmitted between LP 102, 104 and synchronize programmer to implant communication such that programmer 109 does not transmit communications signals 113 until after an implant to implant messaging sequence is completed.

In accordance with embodiments, LP 102, 104 may combine transmit operations with therapy. The transmit event marker may be configured to have similar characteristics in amplitude and pulse width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse width. The foregoing pacing parameters correspond to a current draw of about 1.9 µA. The same LP 102, 104 may implement an event message utilizing event signaling parameters for amplitude, pulse width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102, 104 senses an intrinsic event, the transmitter sends a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, LP 102, 104 may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102, 104 increases an extent to which LP 102, 104 uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25V pace pulse would save 1.5 µA of pacing current budget. With lower pulse amplitudes, LP 102, 104 may use larger pulse widths.

By combining event messages and low power pacing, LP 102, 104 may realize additional longevity. Today longevity standards provide that the longevity to be specified based on a therapy that utilizes 2.5V amplitude, 0.4 ms pulses at 100% pacing. Optionally, a new standard may be established based on pacing pulses that deliver lower amplitude and/or shorter pacing pulses.

In an embodiment, a communication capacitor is provided in LP 102, 104. The communication capacitor may be used to transmit event signals having higher voltage for the event message pulses to improve communication, such as when the LPs 102 and 104 experience difficulty sensing event messages. The high voltage event signaling may be used for implants with high signal attenuation or in the case of a retry for an ARQ (automatic repeat request) handshaking scheme.

For example, when an LP 102, 104 does not receive an event message within a select time out interval, LP 102, 104 may resend an event message at a higher amplitude. As another example, LP 102, 104 may perform an event signaling auto-level search wherein the LPs send event messages at progressively higher amplitude until receiving confirmation that an event message was received (or receiving a subsequent event message from another LP). For example, in DDD mode when the atrial or ventricular LP 102, 104 does not see an event signal from LP 102, 104 in the other chamber before its timeout interval it could automatically raise the amplitude of the event message, until the LPs 102 and 104 become and remain in sync. Optionally, LP 102, 104 may implement a search hysteresis algorithm similar to those used for rate and amplitude capture to allow the lowest safe detectible amplitude to be determined.

The LPs 102 and 104 may be programmable such as to afford flexibility in adjusting the event marker pulse width. In some embodiments, different receiver circuits may be provided and selected for certain pulse widths, where multiple receivers may be provided on a common ASIC, thereby allowing the user to vary the parameters in an LP after implant.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to leadless cardiac pacemaker 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102, 104 configured for implantation in electrical contact with a cardiac chamber and configured to perform cardiac pacing functions in combination with the co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
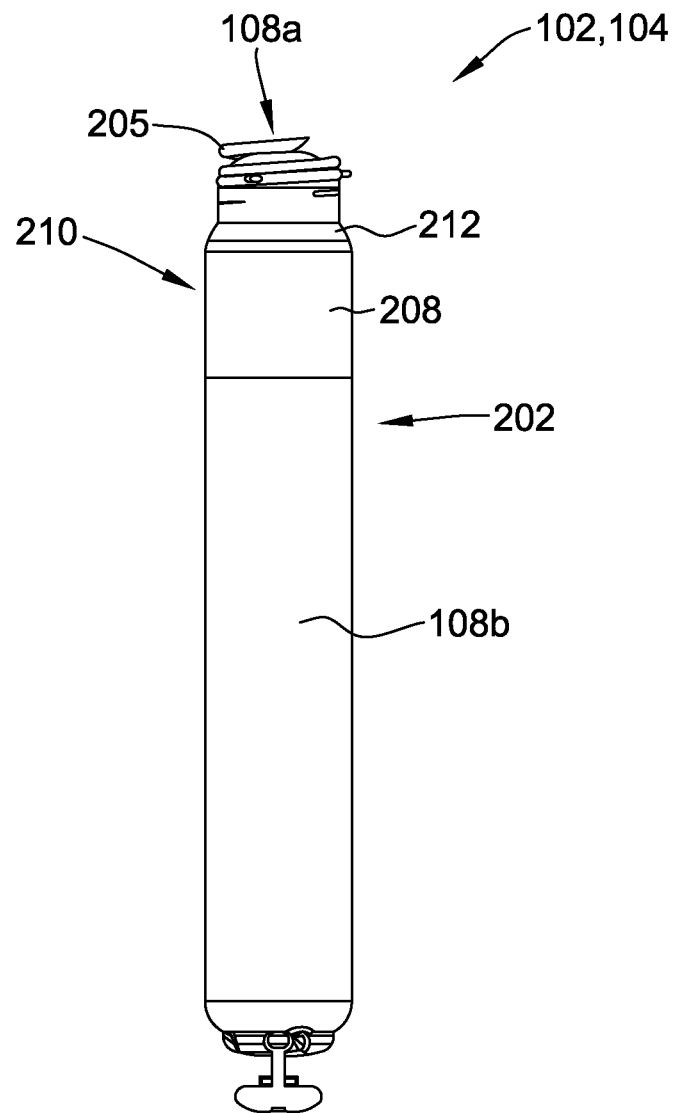
FIG. 3 illustrates a LP in accordance with embodiments herein.

FIG. 3 shows a LP 102, 104. The LP can include a hermetic housing 202 with electrodes 108*a* and 108*b* disposed thereon. As shown, electrode 108*a* can be separated from but surrounded partially by a fixation mechanism 205, and the electrode 108*b* can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108*a* and 108*b*. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108*a* and 108*b*. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108*a* and 108*b*. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108*a* and 108*b* can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108*a* can be a pace/sense electrode and electrode 108*b* can be a return electrode. The electrode 108*b* can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108*a* in FIG. 3) into contact with stimulable tissue. Electrode 108*b* can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In one embodiment, LP 102, 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with an embodiment, a method is provided for coordinating operation between first and second leadless pacemakers (LPs) configured to be implanted entirely within first and second chambers of the heart. The method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 4:
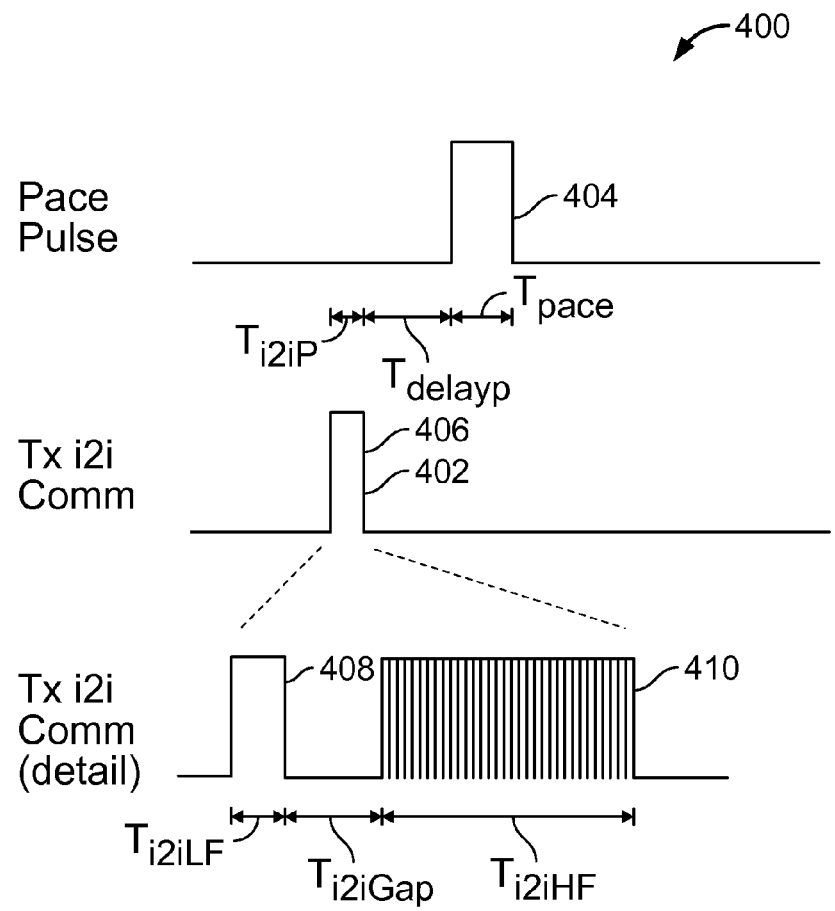
FIG. 4 is a timing diagram demonstrating one embodiment of implant to implant (i2i) communication for a paced event.

FIG. 4 is a timing diagram 400 demonstrating one example of an i2i communication for a paced event. The i2i communication may be transmitted, for example, from LP 102 to LP 104. As shown in FIG. 4, in this embodiment, an i2i transmission 402 is sent prior to delivery of a pace pulse 404 by the transmitting LP (e.g., LP 102). This enables the receiving LP (e.g., LP 104) to prepare for the remote delivery of the pace pulse. i2i transmission 402 includes an envelope 406 that may include one or more individual pulses. For example, in this embodiment, envelope 406 includes a low frequency pulse 408 followed by a high frequency pulse train 410. Low frequency pulse 408 lasts for a period $T_{i2iLF}$, and high frequency pulse train 410 lasts for a period $T_{i2iHF}$. The end of low frequency pulse 408 and the beginning of high frequency pulse train 410 are separated by a gap period, $T_{i2iGap}$.

As shown in FIG. 4, i2i transmission 402 lasts for a period $T_{i2iP}$, and pace pulse 404 lasts for a period $T_{pace}$. The end of i2i transmission 402 and the beginning of pace pulse 404 are separated by a delay period, $T_{delayP}$. The delay period may be, for example, between approximately 0.0 and 10.0 milliseconds (ms), particularly between approximately 0.1 ms and 2.0 ms, and more particularly approximately 1.0 ms.

Figure 5:
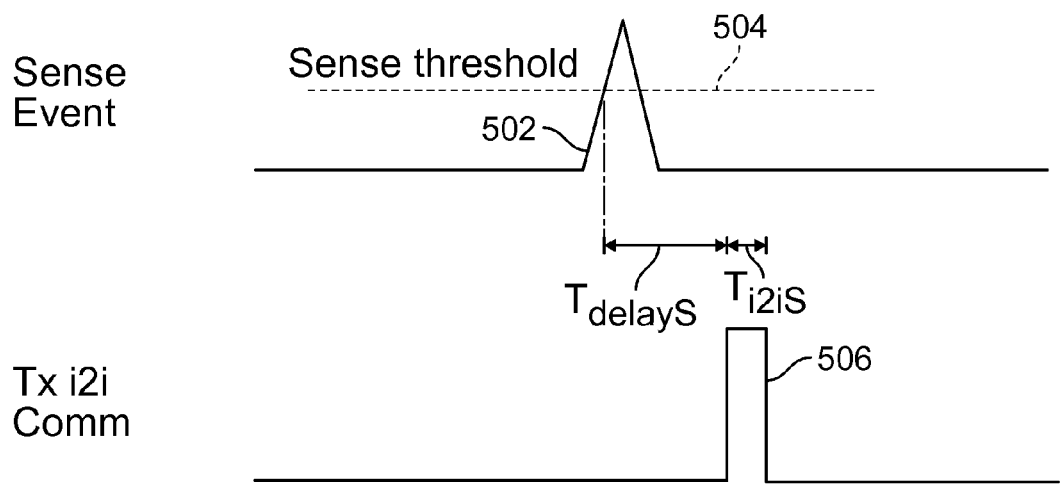
FIG. 5 is a timing diagram demonstrating one embodiment of i2i communication for a sensed event.

FIG. 5 is a timing diagram 500 demonstrating one example of an i2i communication for a sensed event. The i2i communication may be transmitted, for example, from LP 102 to LP 104. As shown in FIG. 5, in this embodiment, the transmitting LP (e.g., LP 102) detects the sensed event when a sensed intrinsic activation 502 crosses a sense threshold 504. A predetermined delay period, $T_{delayS}$, after the detection, the transmitting LP transmits an i2i transmission 506 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 402, i2i transmission 506 may include an envelope that may include one or more individual pulses. For example, similar to envelope 406, the envelope of i2i transmission 506 may includes a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB<br>Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB<br>Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communications, in order to provide safer therapy. For example, in the event that LP to LP (i2i) communications are lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communications to perform ventricular pace/sense activities. Once i2i communications are restored, the system 100 can automatically resume dual-chamber functionalities.

Forward Arming

Optionally, the system 100, while maintaining the master/slave configuration may operate in a mode referred to as "forward arming". During forward arming, each of the aLP and vLP set certain event-to-event timers and take select actions during subsequent cardiac cycles when the corresponding event-to-event timers "time out" or expire without the corresponding aLP and vLP receiving a new event message from the other aLP or vLP. By way of example, an atrial LP may set an atrial to atrial escape interval (AAEI) timer based on a predetermined or programmed interval (e.g., a base rate), an interval modulated by a sensor output (e.g., rate-responsive intervals), a time between prior successive atrial events (intrinsic or paced), etc. When the atrial LP does not receive a new event marker from the ventricular LP before expiration of the AAEI timer, the atrial LP will undertake an appropriate action based on its forward arming setting or status (e.g. reset other timers, deliver an atrial paced event, etc.). A ventricular LP may set a ventricular to ventricular escape interval (VVEI) timer based on a predetermined or programmed interval (e.g., a base rate), an interval modulated by a sensor output (e.g., rate-responsive intervals), a time between prior successive ventricular events (intrinsic or paced), etc. When the ventricular LP does not receive a new event marker from the atrial LP before expiration of the VVEI timer, the ventricular LP will undertake an appropriate action based on its forward arming settings or status (e.g. reset other timers, deliver a ventricular paced event, etc.).

In a "pure" master/slave configuration (without forward arming), a ventricle to atrium ("V2A") AP command marker (to command the aLP to immediately deliver an atrial pace pulse) may be transmitted from the vLP at a time when the ventricle may be in a vulnerable period. While the signals used in i2i communications are designed to limit the possibility of inadvertent excitation of underlying tissue due to event messages, using forward arming with "VP" and "VS" event markers (which are transmitted substantially concurrent with a ventricular pace pulse and sense event, respectively), instead of relying solely on AP command markers, further limits the possibility of inadvertent excitation. Using forward arming with event markers, the vLP may still run all dual-chamber algorithms and remain the "master" device, while the aLP may still remain the "slave" device. Importantly, with forward arming, the vLP can (except as noted below) orchestrate all decision-making and timings (including, for example, rate-response rate changes).

In alternative embodiments, some dual-chamber algorithms could be managed directly by the aLP. For example, as atrial tachycardia/fibrillation is an atrial-specific dysrhythmia, it might be desirable for Auto Mode Switching (AMS) to be managed directly by the aLP. As a corollary of such a decision to have the aLP manage AMS, AS markers would not necessarily need to be transmitted to the vLP during AMS. Similarly, the aLP also may not need to transmit AS markers to the vLP during PVARP or other atrial refractory periods.

Optionally, the i2i communication markers may be emitted substantially concurrent with a local pace or sense event. As such, there is no risk of emitting a marker during a vulnerable period, and thus no risk of inducing unintended excitations.

With forward arming, instead of the vLP commanding the aLP to immediately deliver a pacing pulse (as in a strict master/slave configuration), each "VS" or "VP" V2A event marker received by the aLP effectively "arms" or resets certain timers within the aLP, where the aLP delivers a pacing pulse after the expiration of the next appropriate VA interval (unless inhibited by a sensed intrinsic atrial event), as described herein. The term i2i marker includes all markers that may be sent between two or more implantable devices (e.g., LP to LP, ICD to LP, LP to ICD). The term V2A event marker includes all event related markers that may be sent from a vLP to an aLP.

With forward arming, the aLP will not deliver any pacing pulse unless/until the aLP is "armed" via the receipt of a V2A event marker. As such, in the face of any breakdown in i2i communications (transient or prolonged), the system 100 will inherently revert to safe ventricular-based pace/sense functionalities (since the vLP device is managing the algorithms, such that its pace/sense activities do not depend on i2i communication).

An extension of the forward arming process enables the aLP to "bridge" one or more missed/corrupted V2A markers by extending the arming permission for n future cardiac cycles (with no bridging, next "n" pace requests=1).

Figure 6:
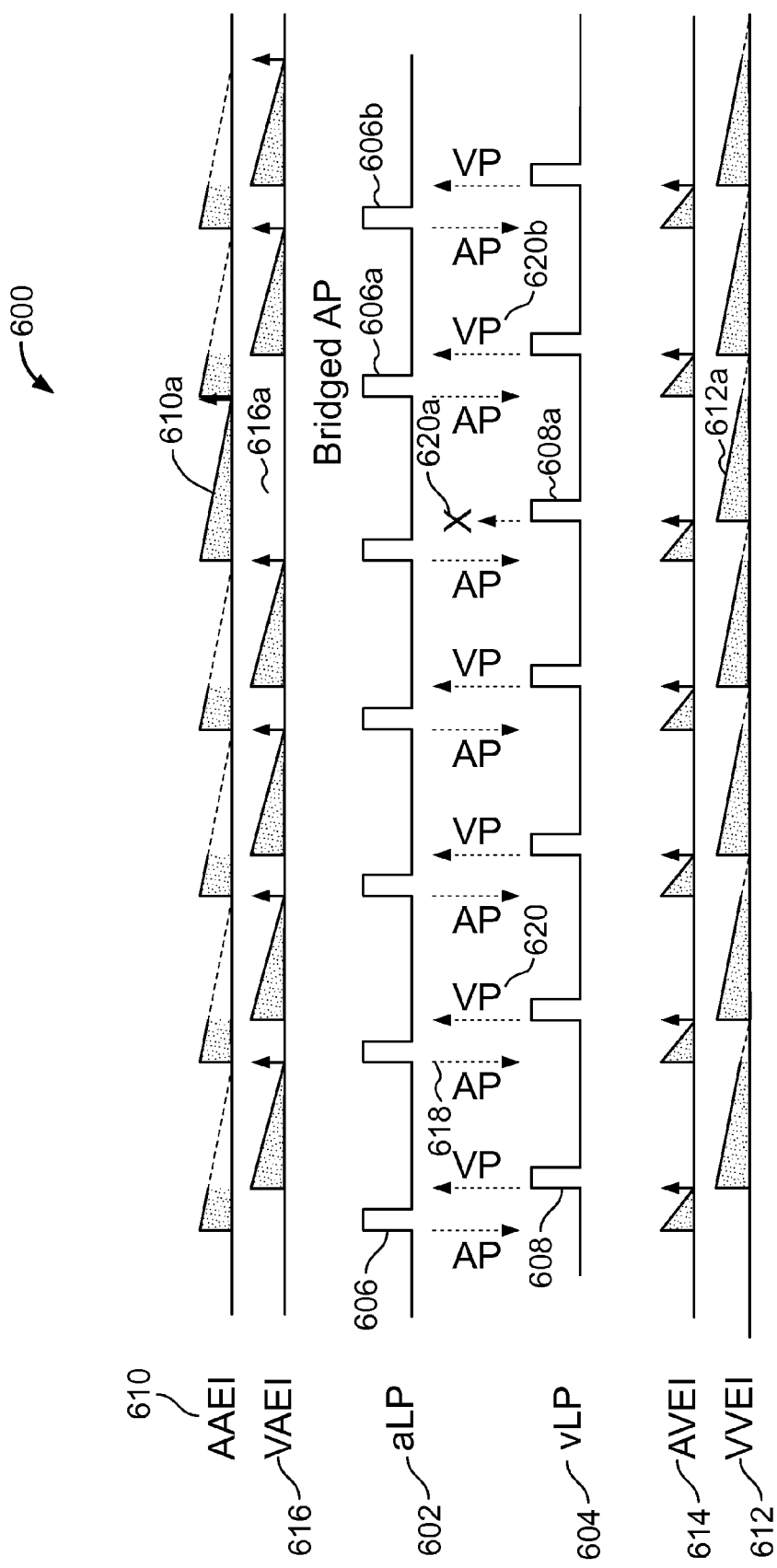
FIG. 6 is a timing diagram illustrating operation of an atrial leadless pacemaker (aLP) and a ventricular leadless pacemaker (vLP) communicating with one another in accordance with one embodiment of a forward arming algorithm.

For example, FIG. 6 is a timing diagram 600 illustrating operation of an aLP 602 and a vLP 604 communicating with one another in accordance with a forward arming algorithm. aLP 602 may be, for example, LP 102 (shown in FIG. 1), and vLP 604 may be, for example, LP 104 (shown in FIG. 1). In diagram 600, aLP 602 generates atrial pacing pulses 606 and vLP 604 generates ventricular pacing pulses 608. For clarity, diagram 600 includes only pace events, and does not show any sense events. Further, forward arming algorithms may also incorporate variable rate changes, as described below. Again, for clarity, diagram 600 does not demonstrate variable rate changes.

In this embodiment, in accordance with the forward arming algorithm, aLP 602 initiates and manages atrial-to-atrial escape intervals (AAEIs) and ventricular-to-atrial escape intervals (VAEIs). Further, vLP 604 initiates and manages atrial-to-ventricular escape intervals (AVEIs) and ventricular-to-ventricular escape intervals (VVEIs).

For atrial pacing pulses 606 (i.e., an atrial pulse event), aLP 602 transmits a corresponding marker ("AP") 618 to vLP 604. Concurrently, aLP 602 initiates an AAEI timer 610. If vLP 604 does not manage PVARP (e.g., aLP 602 handles PVARP), then in response to receiving an "AP" event marker 618, vLP 604 initiates a PAVB interval (not shown), vLP 604 cancels a VVEI timer 612, and vLP 604 initiates an AVEI timer 614. Alternatively, if vLP 604 does manage PVARP, then in response to receiving an "AP" event marker 618, vLP 604 initiates a PAVB interval (not shown), vLP 604 cancels a VVEI timer 612, and vLP 604 initiates an AVEI timer 614P when vLP 604 determines that the cardiac cycle is not currently in a PVARP. In certain embodiments, VVEI and AVEI timers may be separate distinct timers. In certain embodiments, VVEI and AVEI timers are managed and/or initiated via a single timer.

For ventricular pacing pulse 608 (e.g., a ventricular pace event), vLP 604 transmits a corresponding marker ("VP") 620 to aLP 602. Concurrently, vLP 604 initiates VVEI timer 612. Furthermore, in response to receiving a "VP" event marker 620, aLP 602 initiates PVAB and PVARP intervals (not shown), aLP 602 cancels AAEI timer 610, and aLP 602 initiates a VAEI timer 616. In certain embodiments, AAEI and VAEI timers are separate and distinct timers. In certain embodiments, AAEI and VAEI timers are managed via a single timer by, for example, lengthening or shortening the AA escape interval to match that implied by the VAEI.

Diagram 600 illustrates operation of aLP 602 and vLP 604 under these conditions. Notably, solid vertical arrows in diagram 600 indicate expiration of the associated escape interval timer and an associated request for the associated LP to deliver a pacing pulse.

Diagram 600 also illustrates the result of a VP marker 620a transmitted from vLP 604 failing to be successfully received by aLP 602 (e.g., because of signal interference, extrinsic noise, high signal attenuation, etc). Specifically, ventricular pacing pulse 608a is delivered by vLP 604, and in response, vLP 604 initiates VVEI timer 612a. However, because VP marker 620 does not reach aLP 602, aLP 602 does not cancel AAEI timer 610a or initiate VAEI timer 616a. With atrial bridging enabled, aLP 602 may still generate atrial pacing pulse 606a when AAEI timer 610a expires.

In this embodiment, aLP 602 has arming permission to bridge one extra cycle without receipt of an immediately preceding V2A marker (i.e., next "n" pace requests=2). Accordingly, if VP marker 620b, immediately subsequent to VP marker 620a, also failed to reach aLP 602, aLP 602 would not issue another atrial pacing pulse 606b to "bridge" that subsequent cycle. However, in other embodiments, aLP 602 may have an arming permission for any number of future cycles (e.g., n=3, n=5, n=10, etc.).

Figure 7:
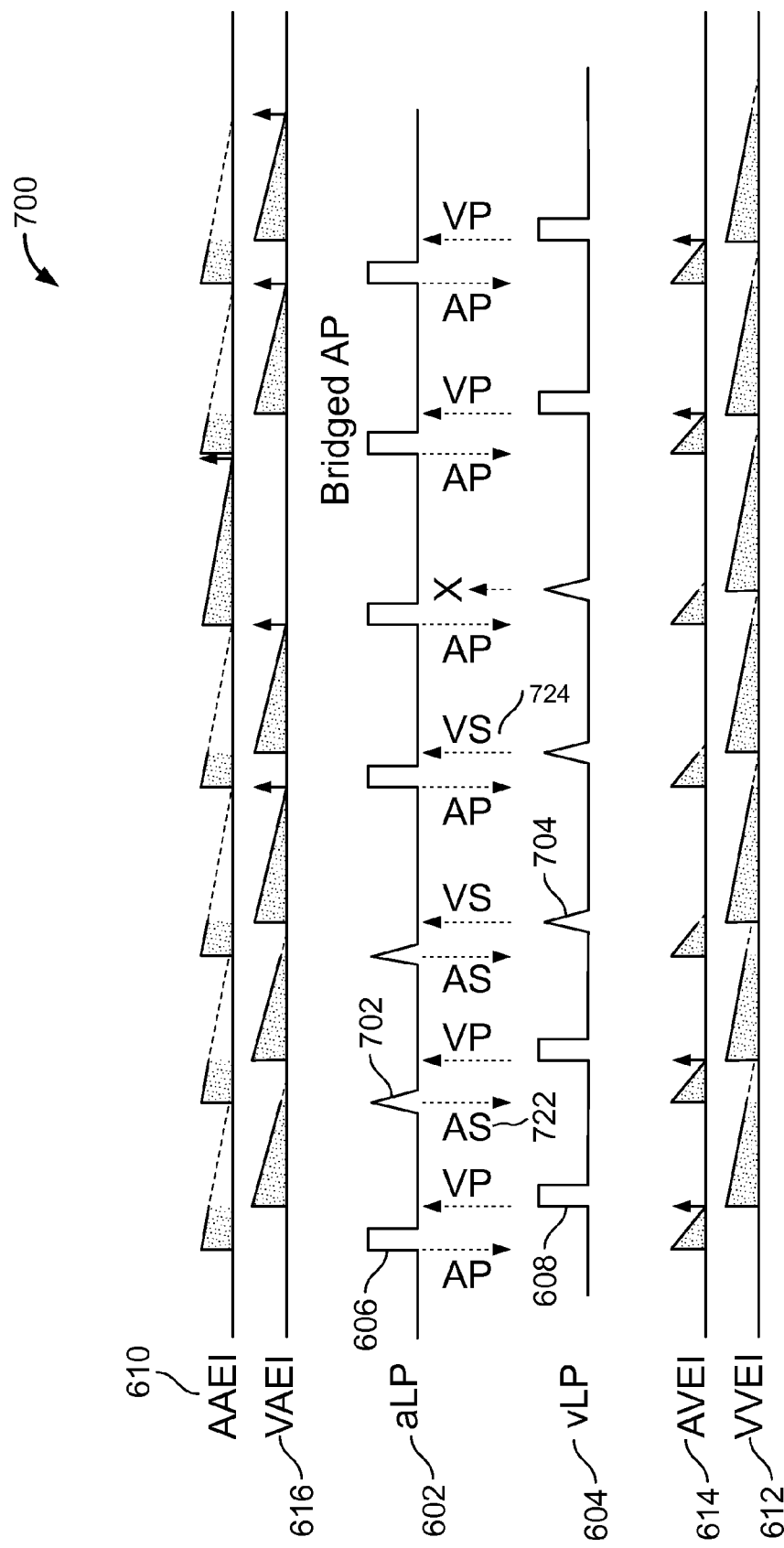
FIG. 7 is a timing diagram illustrating further operation of an aLP and a vLP in accordance with the forward arming algorithm shown in FIG. 6

FIG. 7 is a timing diagram 700 illustrating further operation of aLP 602 and vLP 604 in accordance with the forward arming algorithm. Relative to timing diagram 600 (shown in FIG. 6), timing diagram 700 also includes atrial sensed events 702 and ventricular sensed events 704. Otherwise, timing diagram 700 is substantially similar to timing diagram 600.

For atrial sensed event 702, aLP 602 transmits a corresponding marker ("AS") 722 to vLP 604. Concurrently, aLP 602 initiates AAEI timer 610 and aLP 602 cancels VAEI timer 616. If vLP 604 does not manage PVARP (e.g., aLP 602 handles PVARP), then in response to receiving an "AS" event marker, vLP 604 cancels VVEI timer 612, and vLP 604 initiates AVEI timer 614. Alternatively, if vLP 604 does manage PVARP (e.g., aLP 602 handles PVARP), then in response to receiving an "AS" event marker, vLP 604 cancels VVEI timer 612, and vLP 604 initiates AVEI timer 614 when vLP 604 determines that the cardiac cycle is not currently in a PVARP.

For ventricular sensed event 704, vLP 604 transmits a corresponding marker ("VS") 724 to aLP 602. Concurrently, vLP 604 initiates VVEI timer 612 and vLP 604 cancels AVEI timer 614. Furthermore, in response to receiving "VS" event marker 724, aLP 602 initiates a PVARP interval (not shown), aLP 602 cancels AAEI timer 610, and aLP 602 initiates VAEI timer 616.

Figure 8:
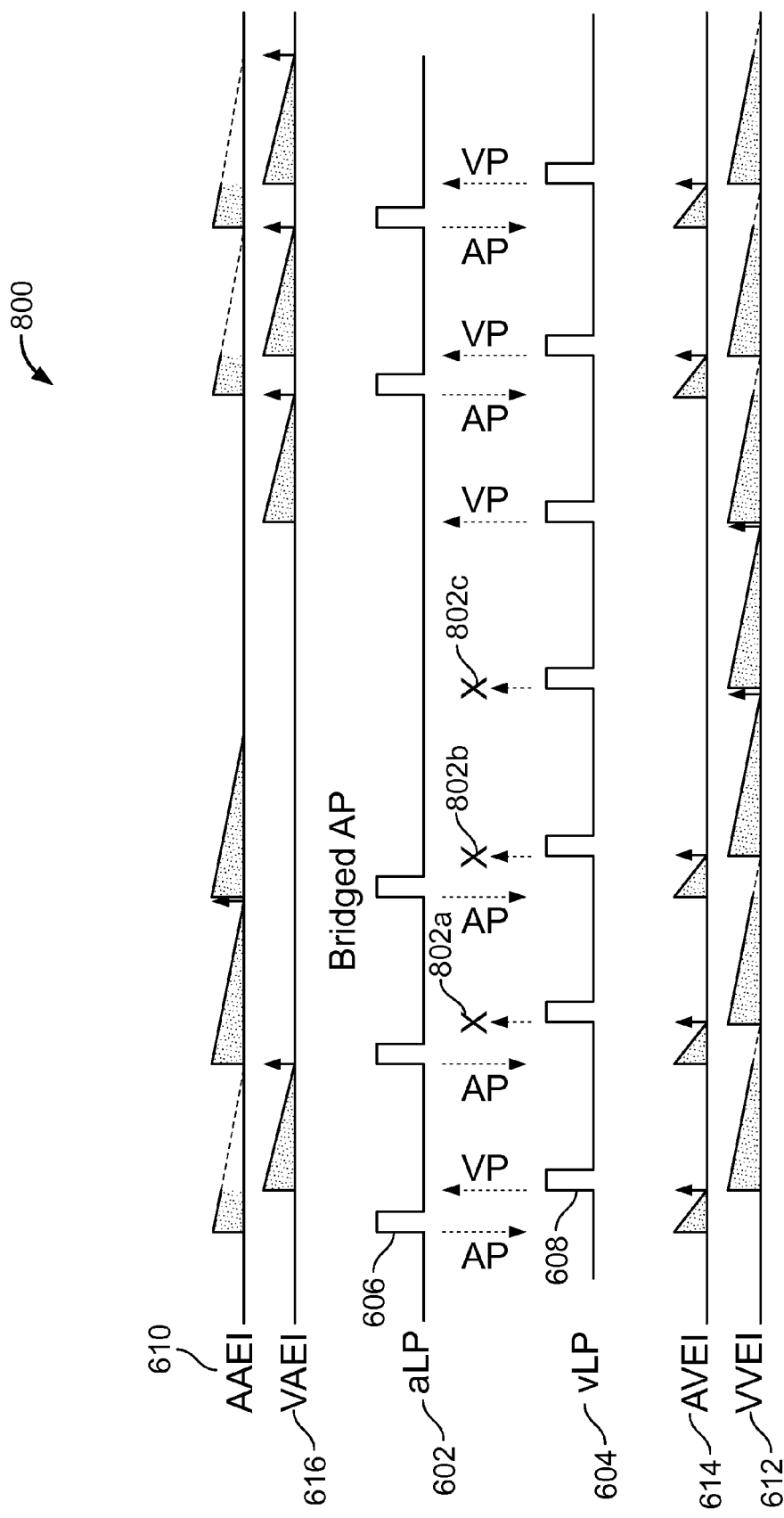
FIG. 8 is a timing diagram illustrating operation of an aLP and a vLP when multiple subsequent markers fail to reach the aLP.

FIG. 8 is a timing diagram 800 illustrating operation of aLP 602 and vLP 604 when multiple subsequent VP markers fail to reach aLP 602. As noted above, in this embodiment, aLP 602 has arming permission for one additional cycle (i.e., n=2). Accordingly, aLP 602 re-arms after a first failed VP marker communication 802a, but does not re-arm after second and third failed VP marker communications 802b and 802c. This results in the absence of atrial pacing pulse 606 for multiple cycles. As explained above, in other embodiments, aLP 602 may have an arming permission for any number of future cycles (e.g., n=3, n=5, n=10, etc.) to prevent the missed atrial pacing pulses.

In this embodiment, aLP 602 re-arms in response to receiving each individual successful V2A marker (e.g., VP marker or VS marker). Alternatively, aLP 602 may only re-arm in response to receiving a predetermined number of multiple consecutive successful V2A markers (e.g., two successful V2A markers, three successful V2A markers, etc.) This causes aLP 602 to re-arm only after some modicum of stability in i2i communications between aLP 602 and vLP 604 has been demonstrated.

Figure 9:
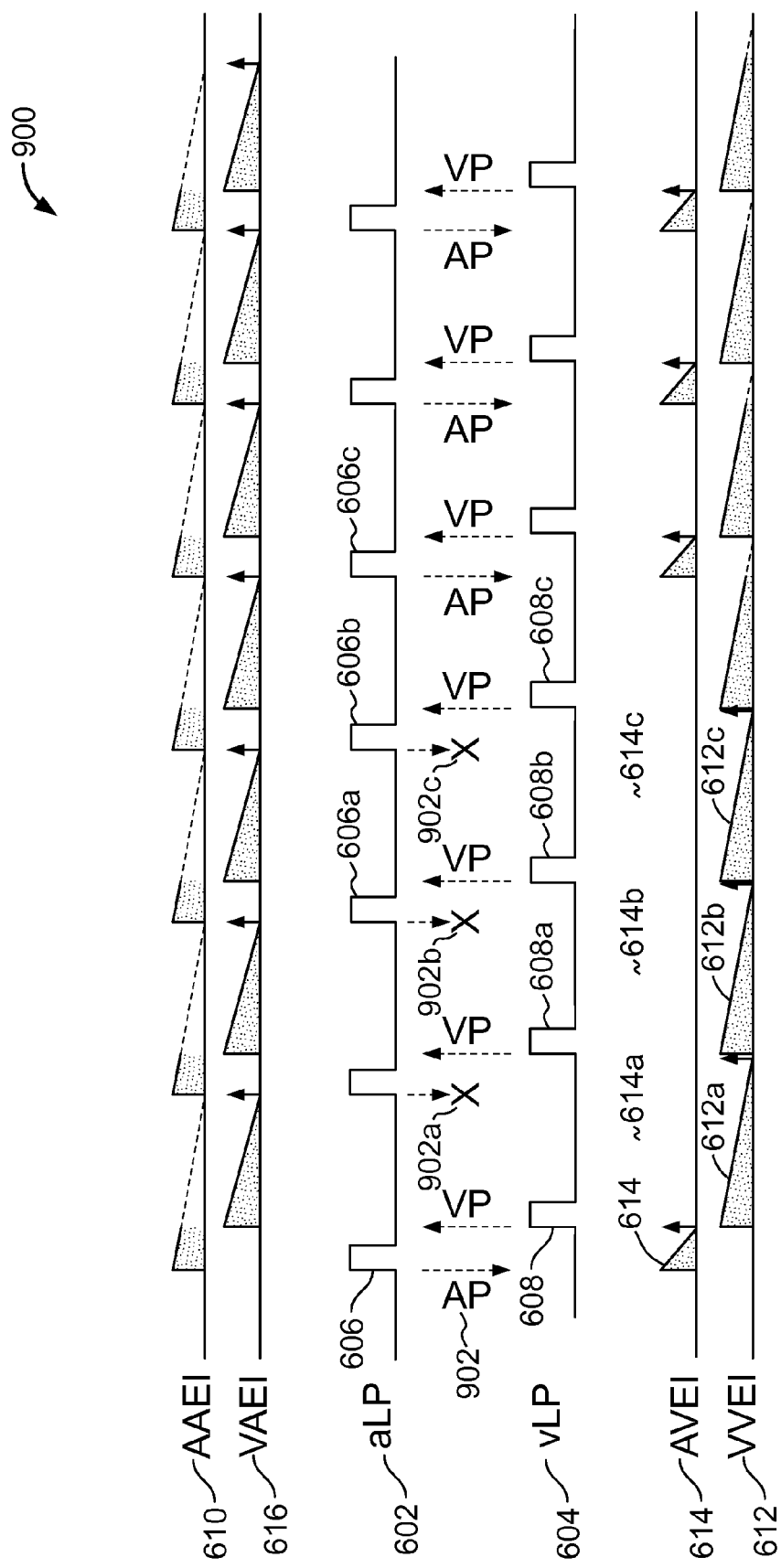
FIG. 9 is a timing diagram illustrating operation of an aLP and a vLP when multiple subsequent markers fail to reach the vLP.

FIG. 9 is a timing diagram 900 illustrating operation of aLP 602 and vLP 604 when multiple subsequent AP markers 902 fail to reach vLP 604. As shown in FIG. 9, despite AP markers 902a, b, and c failing to reach vLP 604, all pacing pulses are still delivered (i.e., atrial pacing pulses 606a, b, and c and ventricular pacing pulses 608a, b, and c are delivered every cycle). However, for cycles where AP markers 902a, b, and c do not reach vLP 604, AVEI timer 614*a, b,* and *c* are not reinitiated, and so ventricular pacing pulses 608*a, b,* and *c* are delivered on each expiration of VVEI timer 612*a, b,* and *c*.

Figure 10:
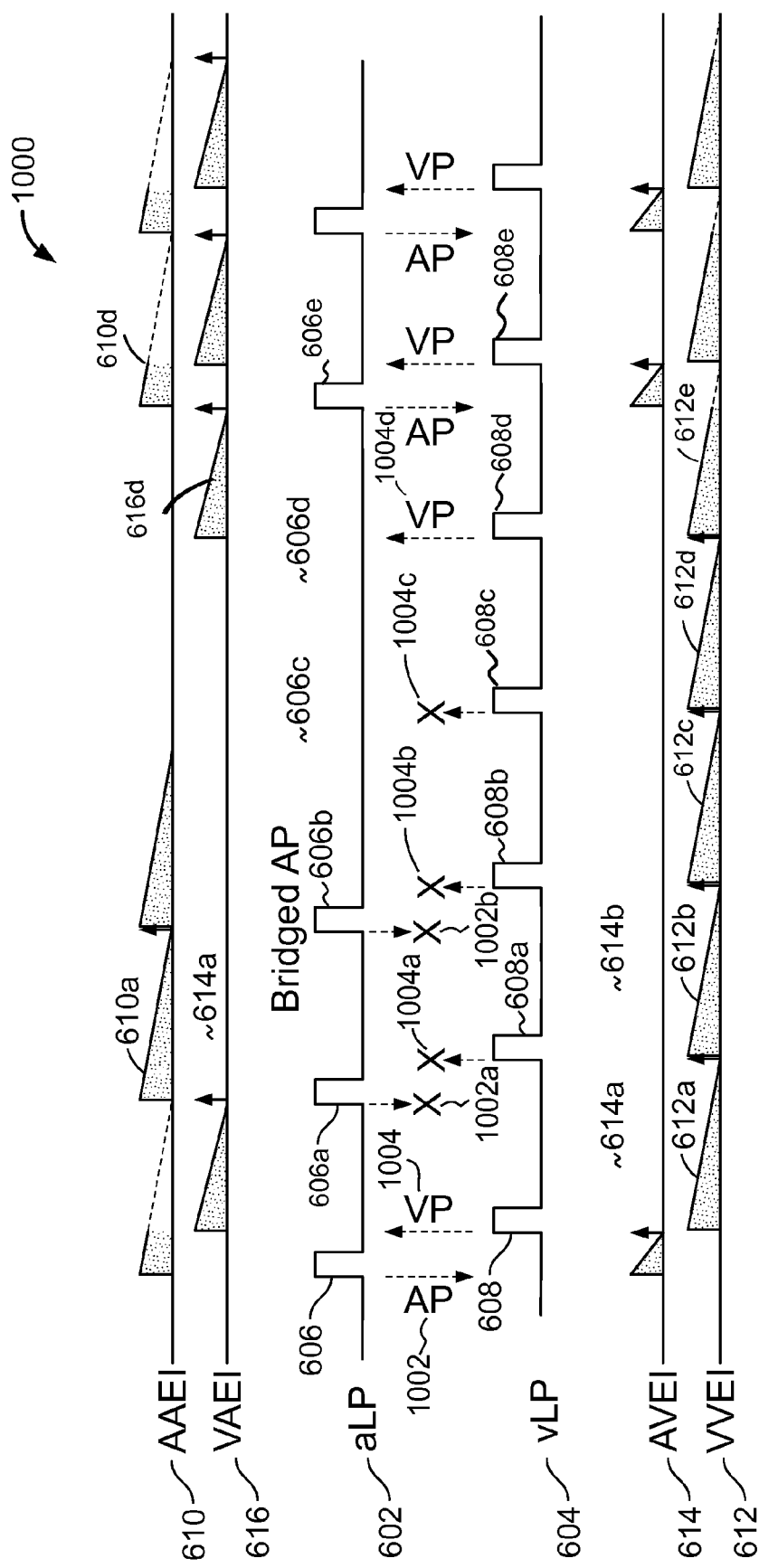
FIG. 10 is a timing diagram illustrating operation of an aLP and a vLP when markers fail to reach the vLP and the aLP.

FIG. 10 is a timing diagram 1000 illustrating operation of aLP 602 and vLP 604 when both AP marker 1002 fails to reach vLP 604 and VP marker 1004 fails to reach aLP 602. This may be referred to as a bi-directional failure of i2i communications. As shown in FIG. 10, for any and all cycles in which an A2V event message is not received from the aLP, ventricular pacing pulses are still delivered every cycle upon each expiration of the associated VVEI timer. For example, as shown in FIG. 10, despite AP markers 1002*a* and *b* failing to reach vLP 604 and despite aLP withholding the transmission of markers for some subsequent cardiac cycles (e.g., when aLP inhibits atrial pacing pulses 606 *c* and *d*), ventricular pacing pulses 608 are still delivered every cycle, e.g., 608*a, b, c,* and *d*.

However, for cycles where AP markers are not received by vLP 604, e.g., 606*a*, 606*b*, 606*d*, AVEI timer 614*a* and *b* are not reinitiated, and so ventricular pacing pulses 608*a, b, c,* and *d* are delivered on each expiration of VVEI timer 612*a, b, c,* and *d*.

And despite VP marker 1004*a* failing to reach aLP 602, atrial pacing pulse 606*a* is still delivered. However, because VP marker 1004*a* does not reach aLP 602, aLP 602 does not cancel AAEI timer 610*a* or initiate VAEI timer 616*a*. With atrial bridging enabled, aLP 602 may still generate atrial pacing pulse 606*a* when AAEI timer 610*a* expires.

In this embodiment, aLP 602 has arming permission to bridge one extra cycle without receipt of an immediately preceding V2A marker (i.e., n=2). Accordingly, since VP markers 1004*b* and *c*, immediately subsequent to VP marker 1004*a*, also fail to reach aLP 602, aLP 602 does not issue atrial pacing pulse 606*c* and *d* to "bridge" those subsequent cycles.

When VP marker 1004*d* reaches aLP 602, the arm command included with VP marker 1004*d* re-arms aLP 602 by re-initiating timer VAEI 616*d*, therein enabling aLP 602 to generate atrial pacing pulse 606*e* when VAEI timer 616*d* expires. aLP 602 also then initiates AAEI timer 610*d* concurrently with atrial pacing pulse 606*e*.

Variable Rate

A feature of cardiac pacemakers is the ability to dynamically vary the pacing rate, such as for rate-responsive pacing. i2i communication can be utilized to manage and coordinate rates and rate changes (or, equivalently, intervals and interval changes) amongst multiple LPs. In a master/slave configuration, the master device may generally determine and dictate the target rate for the system as a whole. In one embodiment, the master device will communicate rate information to the slave device via some or all of its transmitted marker events. For example, if the vLP is the master device and the aLP is the slave device, the vLP may transmit new target rate information to the aLP with each transmitted VS or VP event marker. In one embodiment, that transmitted rate information is a target pacing rate. In an alternative embodiment, that transmitted rate information is a target pacing interval. In yet another embodiment, that transmitted rate information is a change in target rate (or interval) relative to a previous target rate (or interval). In another embodiment, that transmitted rate information is a target interval for a specific timer, such as the VA escape interval timer in the aLP.

This transmitted rate information can either be sent with an event marker as the actual value (to whatever desired precision/significance), or the transmitted rate information can be codified for more efficient transmission. In either case, the transmitted value can represent either an interval (e.g., in msec) or a rate (e.g., in bpm) or a change in interval or rate.

A single event message may have limited payload capacity and thus a single data field may not be able to hold any size rate information value to arbitrary precision. In some embodiments, when the rate information value is too large to be conveyed in a single event message, the rate information value may be partially conveyed in a set of successive event messages corresponding to successive cardiac cycles. This approach may be particularly well suited when transmitting target changes in rate or interval (e.g., delta rate information).

Various coding schemes may be used to convey the delta rate information values during successive cardiac cycles. For example, two exemplary schemes are Powers-of-Two-based or Powers-of-Three based. In the Powers-of-Two based scheme, the code is based on powers of two (e.g., ±1, ±2, ±4, ±8, ±16, . . . , ±2n) or multiples thereof (e.g., ±10, ±20, ±40, etc.). If only one value from the code for the complete delta rate information value can be sent each cardiac cycle, and there is a restriction that the targeted value should not be "overshot" during any adjustment, then the powers-of-two scheme provides a code-efficient means of monotonically reaching any arbitrary value over a minimal number of cycles. Thus, for example, a target value of +60 can be achieved via a monotonic asymptotic approach as 32+16+8+4 (i.e., over four cycles). In the Powers-of-Three based, the code for the complete delta rate information value is based on powers of three (e.g., ±1, ±3, ±9, ±27, . . . , ±3n) or multiples thereof (e.g., ±10, ±30, ±90, etc.). If only one value from the code for the complete delta rate information value can be sent each cycle, and there is no "monotonicity" restriction during adjustments, then this powers-of-three scheme provides a code-efficient means of reaching any arbitrary value over a minimal number of cycles. Thus, for example, a target value of +60 can be achieved via a non-monotonic asymptotic approach as 81−27+9−3 (i.e., over four cycles).

Most DDD(R) devices use so-called atrial-based timing, where the overall base rate is governed by (and managed through) the A-A escape interval. However, some pacing modes and some pacing situations utilize so-called ventricular-based timing, where the overall base rate is governed by (and managed through) the V-V escape interval. Both approaches can be effectively managed via forward arming from a vLP master device to an aLP slave device in which rate (or interval) information is also transmitted with some or all V2A event markers. For example, a vLP may transmit to an aLP a target pacing rate. To achieve atrial-based timing, the aLP can calculate an appropriate VA escape interval timer duration as the difference between the newly-received rate information (converted, as appropriate, to a target AA interval) and the just-completed AV interval duration. Alternatively, to approximate ventricular-based timing, the aLP can calculate an appropriate VA escape interval timer duration as the difference between the newly-received rate information (converted, as appropriate, to a target AA interval) and the programmed AV escape interval (adjusted, as appropriate, for rate-responsiveness). In another embodiment, a vLP may transmit to an aLP a target VA escape interval timer value directly, in which the vLP calculates this target VA escape interval timer value using equivalent atrial-based or ventricular-based methods described above. In yet another embodiment, the aLP may make direct adjustments to an active AA escape interval timer rather than utilize a separate VA escape interval timer.

Figure 11:
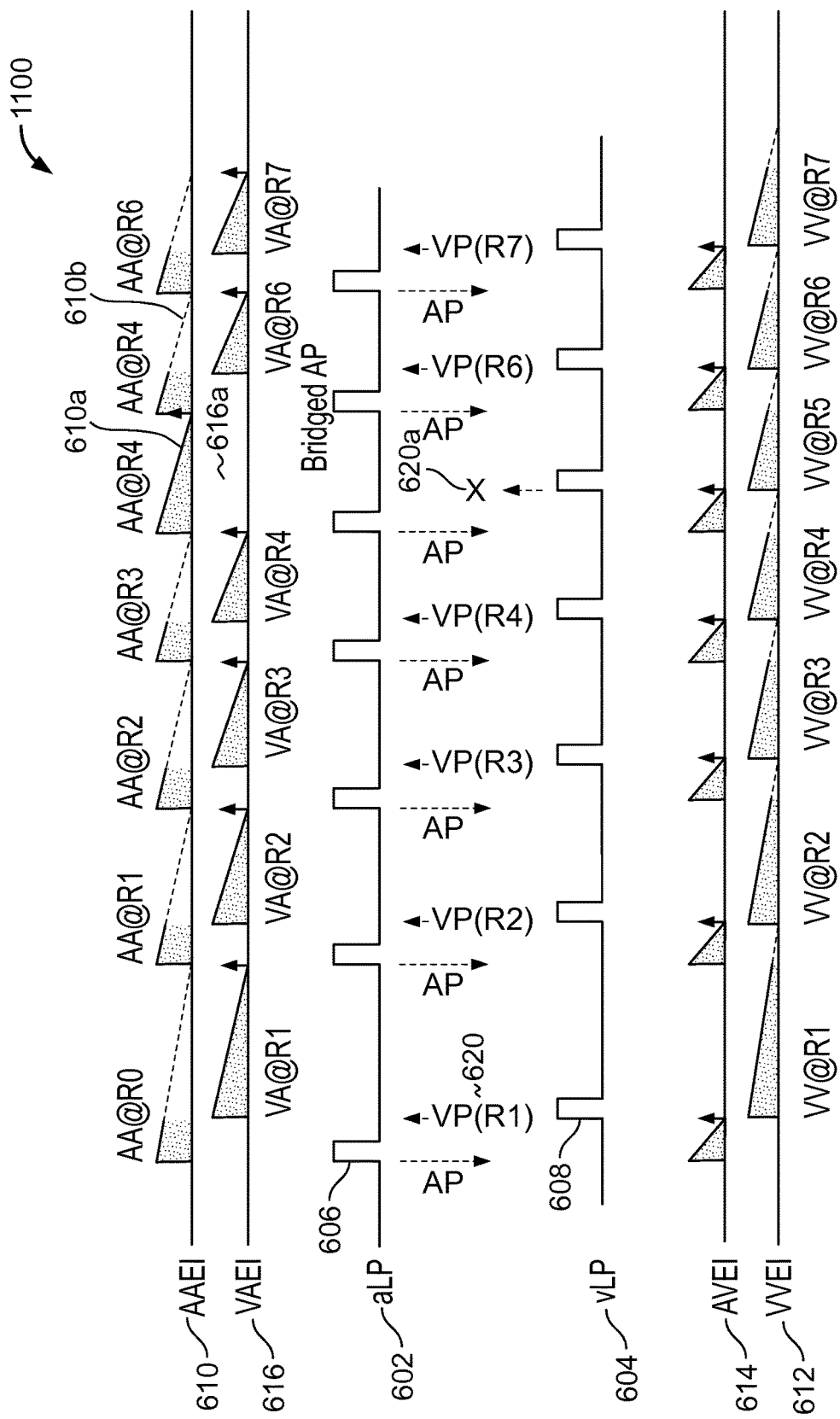
FIG. 11 is a timing diagram illustrating operation of an aLP and a vLP in accordance with one embodiment of a variable rate forward arming algorithm.

FIG. 11 is a timing diagram 1100 illustrating operation of aLP 602 and vLP 604 in accordance with a variable rate forward arming algorithm. Timing diagram 1100 is similar to timing diagram 600 (shown in FIG. 6). However, in timing diagram 1110, VP markers 620 include rate information to be transmitted from vLP 604 to aLP 602 to adjust the next appropriate VA interval. As described above, the rate information may be a rate value or an interval value or a specific timer value, and furthermore that information may be an absolute value or a relative value. In certain embodiments, AV intervals (e.g., AVEI timer 614) may also be adjusted based on the current rate information.

Specifically, in this embodiment, aLP 602 and vLP 604 use atrial-based ("A-based") timing, where the overall pacing rate is governed through the atrial pacing rate by managing the total A-A interval. In other embodiments, aLP 602 and vLP 604 may use ventricular-based ("V-based") timing, where the overall rate is managed through the total V-V interval. In certain embodiments, both A-based timing and V-based timing may be used and aLP 602 and vLP 604 may switch between the two. The timing base may be selected depending on the active operating mode (e.g., DDD(R) and AAI(R) may use A-based timing, whereas VDD(R) and VVI(R) may use V-based timing). The timing base aLP 602 and vLP 604 may also change transiently depending on certain operating conditions.

As shown in FIG. 11, each VP marker 620 also includes rate information (e.g., R1, R2, R3, etc.). VS markers (if present) would similarly include rate information. Accordingly, in response to each VP marker 620 that reaches aLP 602, the corresponding VAEI timer 616 and following AAEI timer 610 are set according to the received rate information. Further, for failed VP marker 620a, aLP 602 does not cancel AAEI timer 610a or initiate VAEI timer 616a, similar to in timing diagram 600 (shown in FIG. 6). Notably, in this embodiment, upon expiry of AAEI timer 610a, aLP 602 paces and starts a subsequent AAEI timer 610b (due to bridging) that is based on the same rate information (i.e., R4) as previous AAEI timer 610a.

In some embodiments, vLP 604 only transmits rate information to aLP 602 if the change in target rate or interval meets or exceeds a predetermined threshold. This predetermined threshold may represent an absolute change in rate or a relative (e.g., percent) change in rate. That is, if the change between the previously transmitted rate and the current target rate is less than the predetermined threshold, no rate information is transmitted. For example, new rate information may not be transmitted until the current target rate differs from the previously transmitted target rate by more than ±5 bpm. The reduced burden of transmitting rate information every cycle may be beneficial to reduce the overall power necessary for i2i transmissions. However, in some embodiments, vLP 604 may transmit rate information to aLP 602 after any failed V2A communication occurs, even if the change in rate is less than the predetermined threshold. vLP 604 may determine that a failed V2A communication occurred, for example, if vLP 604 does not receive an acknowledgement message from aLP 602 in response to attempting to send the V2A communication.

The following Tables 3 and 4 summarize examples of event markers and their associated behaviors in connection with a forward arming configuration.

TABLE 3

"A2V" Markers (i.e., from aLP to vLP)

| Marker | Description | Result in aLP/vLP |
|---|---|---|
| AS | Notification of a sensed event in atrium | aLP: Cancel VAEI timer.<br>aLP: Initiate AAEI timer based on current target rate information.<br>vLP: Cancel VVEI timer.<br>vLP: Initiate AVEI timer based on current target rate information (or initiate AVEI timer when not in PVARP or PVAB). |
| AP | Notification of a paced event in atrium | aLP: Cancel VAEI timer (if still active).<br>aLP: Initiate AAEI timer based on current target rate information.<br>vLP: Initiate PAVB.<br>vLP: Cancel VVEI timer.<br>vLP: Initiate AVEI timer based on current target rate information (or initiate AVEI timer if not in PVARP). |

As shown in Table 3, AS and AP event markers may be sent from an atrial LP to a ventricular LP, when in the forward arming mode. An AS marker is transmitted from an atrial LP when an intrinsic atrial event is sensed. Alternatively, an AP marker is transmitted from an atrial LP when an atrial pacing pulse is generated. In response thereto, the atrial LP cancels the V-to-A escape interval (VAEI) timer and initiates an atrial-to-atrial escape interval (AAEI) timer. The AAEI timer represents a forward arming timer that is set based upon the most-recently determined or acquired (e.g., via V2A i2i communication) target rate information. When the ventricular LP receives an AS or AP marker, the ventricular LP cancels a ventricular-to-ventricular escape interval (VVEI) timer and initiates an atrial-to-ventricular escape interval (AVEI) timer.

Table 4 illustrates examples of VS and VP markers that may be sent from a ventricular LP to an atrial LP based on sensed intrinsic ventricular events or paced ventricular events. When the ventricular LP senses an intrinsic event, the ventricular LP sends a VS marker which is used by the atrial LP to enable arming for one or more intervals. Alternatively, when the ventricular LP generates a ventricular pacing pulse, the ventricular LP sends a VP marker which is used by the atrial LP to enable arming for one or more intervals. The ventricular LP may also include rate information (R) with the VS/VP marker, with that rate information representing absolute or relative adjustments to the target rate or interval, as described in more detail earlier. In response thereto, the atrial LP cancels the AAEI timer, initiates a PVARP interval timer (possibly set based on current target rate information), and initiates a VAEI timer that is set based on transmitted target rate information. In addition, the ventricular LP initiates a VVEI timer based on the same target rate information. When the ventricular LP delivers a paced event, the atrial LP (in response to the VP marker) cancels the AAEI timer, initiates PVAB and PVARP interval timers (possibly set based on current target rate information), and initiates a VAEI timer that is set based on transmitted target rate information. In addition, the ventricular LP initiates a VVEI timer based on the same target rate information.

TABLE 4

"V2A" Markers (i.e., from vLP to aLP)

| Marker | Description | Result in aLP/vLP |
|---|---|---|
| VS(R) | Notification of a sensed event in ventricle Command to enable "arming" of aLP for next pace event (or next n intervals if bridging is enabled), possibly also including new target rate information (R) to adjust next VA escape interval | aLP: Cancel AAEI timer. aLP: Initiate PVARP. aLP: Initiate VAEI timer based on: New target rate information if (R) is included with event marker Last target rate information if no new rate information is included with event marker vLP: Initiate VVEI timer based on target rate information. |
| VP(R) | Notification of a paced event in ventricle Command to enable "arming" of aLP for next pace event (or next n intervals if bridging is enabled), possibly also including new target rate information (R) to adjust next VA escape interval | aLP: Cancel AAEI timer. aLP: Initiate PVAB and PVARP. aLP: Initiate VAEI timer based on: New target rate information if (R) is included with event marker Last target rate information if no new rate information is included with event marker vLP: Initiate VVEI timer based on target rate information. |

Another approach to provide variable rate is to have the vLP adjust the AA interval used by the aLP (instead of the VA). Similar to commanding the VA interval, the vLP commands the AA interval by sending either an absolute value or relative value to change the AA escape interval timer.

In the relative adjustment schemes, where the vLP sends the relative change of rate (or interval) to the aLP, the vLP calculates an appropriate value for relative change (e.g., X). One method for doing this is to subtract an estimate of the actual AA rate from the target rate. The estimate of the AA rate can be derived from the time interval between pairs of A events seen by the vLP (e.g., AS or AP events). However, if there has been a lost A2V marker (indicated by not having the expected A-V-A marker sequence), the actual V-V interval can be used instead. This method of continuously monitoring the AA interval accommodates missed/corrupted V2A markers (which contains the X rate information), as subsequent commands will correct the error. It may be useful to limit the magnitude of the X value to prevent abrupt changes in the atrial rate.

In another approach similar to the one describe above, the AA rate estimate that is used for the X calculation is determined by the vLP by measuring the interval from either an AP or an AS event to an AP event. This more accurately reflects the current AAEI atrial escape interval in the aLP. To prevent the accumulated X value from drifting too far due to lost A2V markers, the accumulated value can be limited.

FIGS. 12-15 are flow charts illustrating operation of aLP 602 and vLP 604 in accordance with certain embodiments of a variable rate forward arming algorithm. In the embodiment illustrated in FIGS. 12-15, the steps depicted occur in sequential order; however, a person of skill in the art after reading the present disclosure will understand that certain blocks may occur in a different order or may occur simultaneously.

In the embodiment illustrated in FIGS. 12-15, as described above, any variable rate information is communicated from vLP 604 to aLP 602, with vLP 604 operating as the "master" and aLP 602 operating as the "slave".

Figure 12:
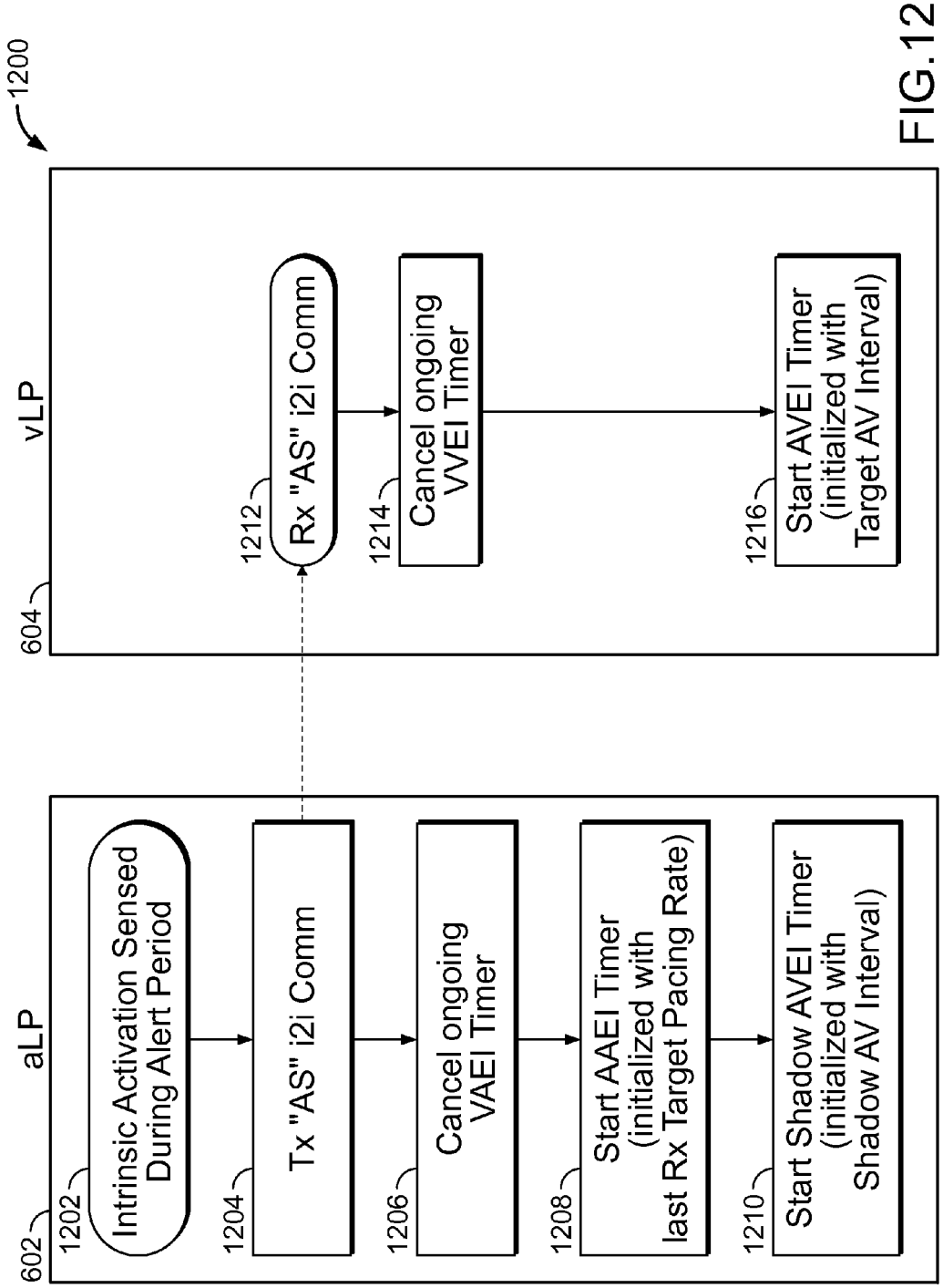
FIG. 12 is a flow chart illustrating operation of an aLP and a vLP during an atrial sense event in accordance with one embodiment.

For example, FIG. 12 is a flow chart 1200 illustrating operation of aLP 602 and vLP 604 upon an atrial sense event. At block 1202, aLP 602 senses an intrinsic activation during an alert period. In response, at block 1204, aLP 602 transmits an AS event marker to vLP 604. aLP 602 also cancels any ongoing VAEI timer 616 at block 1206, and starts an AAEI timer 610 at block 1208. In this embodiment, AAEI timer 610 is initialized based on the last received target rate information. In non-rate-response modes, AAEI timer 610 may alternatively be initialized based directly on a programmed target pacing rate instead of on received target rate information.

aLP 602 may optionally initiate a shadow AVEI timer at block 1210. Shadow AVEI timer parallels AVEI timer 614 of vLP 604 and enables aLP 602 to track operation of vLP 604 even if one or more subsequent V2A signals do not successfully transmit from vLP 604 to aLP 602. For example, the shadow AVEI timer may be used by aLP 602 to initiate a PVARP interval timer even if the expected V2A event marker from vLP 604 is not received by aLP 602. The shadow AVEI timer is initialized with a shadow AV interval, which may be equal to or slightly longer than the target AV interval used in vLP 604.

At block 1212, vLP 604 receives the AS event marker transmitted at block 1204. In response, vLP 604 cancels any ongoing VVEI timer 612 at block 1214, and starts an AVEI timer 614 at block 1216. The AVEI timer 614 is initialized at a target AV interval (e.g., a target sensed AV interval) which may also be adjusted based on the target rate information.

In this embodiment, aLP 602 only transmits the AS marker to vLP 604 when an intrinsic activation is sensed during an alert period. Alternatively, aLP 602 may transmit AS markers even when intrinsic activations are sensed during atrial relative refractory periods as well. In such embodiments, vLP 604 processes the received AS markers appropriately (e.g., by not cancelling or initiating some timers).

Figure 13:
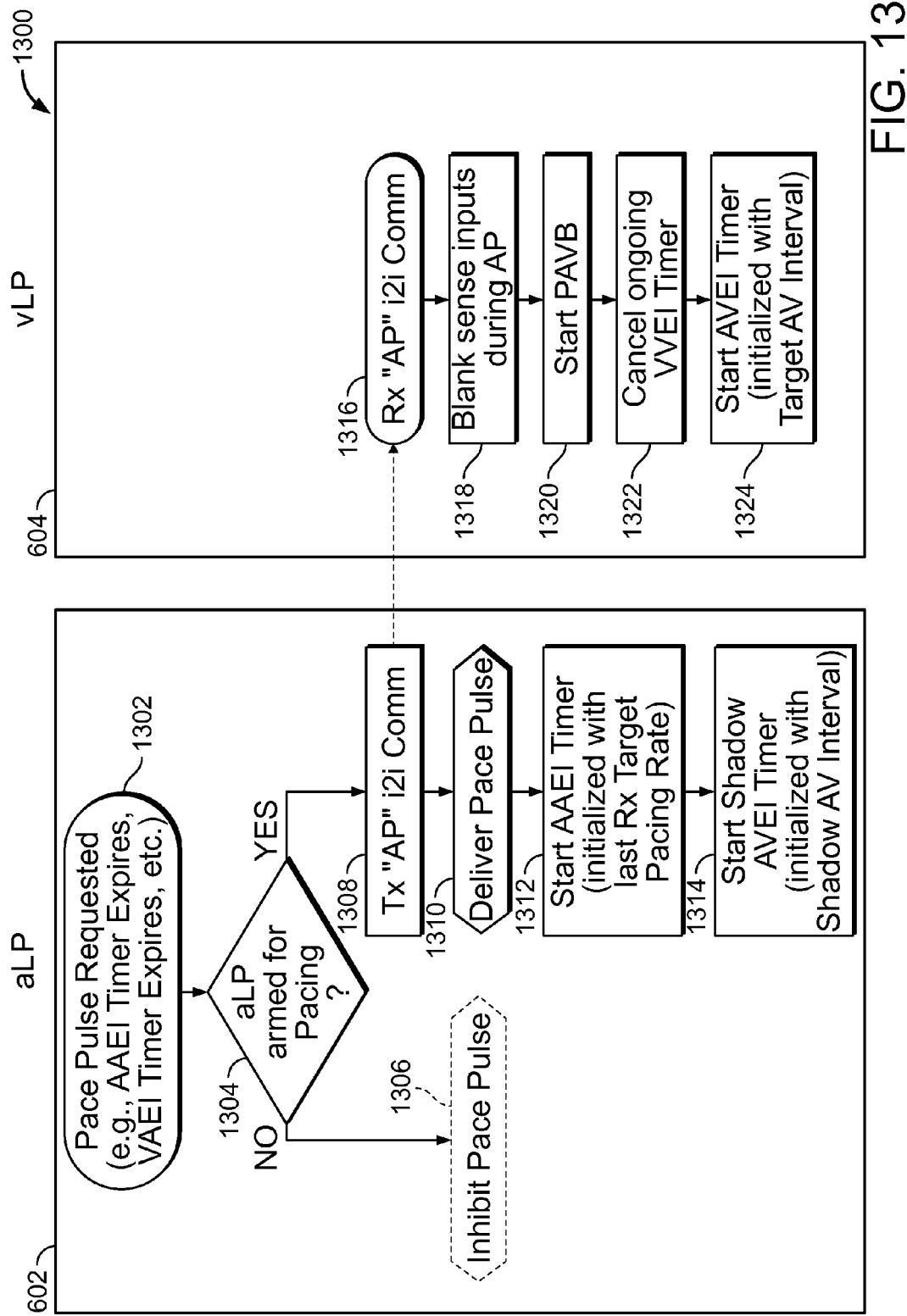
FIG. 13 is a flow chart illustrating operation of an aLP and a vLP during an atrial pace event in accordance with one embodiment.

FIG. 13 is a flow chart 1300 illustrating operation of aLP 602 and vLP 604 upon an atrial pace event. At block 1302, a pace pulse is requested in aLP 602 (e.g., in response to AAEI timer 610 expiring, or VAEI timer 616 expiring, etc.). At block 1304, aLP 602 determines whether aLP 602 is currently armed for pacing. If aLP 602 is not currently armed, flow proceeds to block 1306, and the pace pulse is inhibited. If aLP 602 is armed, flow proceeds to block 1308, and aLP 602 transmits an AP event marker to vLP 604. aLP 602 then delivers the pace pulse at block 1310.

Further, aLP 602 initiates an AAEI timer 610 at block 1312. In this embodiment, AAEI timer 610 is initialized based on the last received target rate information. In non-rate-response modes, AAEI timer 610 may alternatively be initialized based directly on a programmed target pacing rate instead of on received target rate information. aLP 602 may optionally initiate a shadow AVEI timer at block 1314. Shadow AVEI timer parallels AVEI timer 614 of vLP 604 and enables aLP 602 to track operation of vLP 604 even if one or more subsequent V2A signals do not successfully transmit from vLP 604 to aLP 602. For example, the shadow AVEI timer may be used by aLP 602 to initiate PVAB and PVARP interval timers even if the expected V2A event marker from vLP 604 is not received by aLP 602. The shadow AVEI timer is initialized with a shadow AV interval, which may be equal to or slightly longer than the target AV interval used in vLP 604. In the embodiment illustrated in FIG. 13, blocks 1312 and 1314 occur in sequential order; however, in other embodiments, these blocks may occur in any order or may occur simultaneously.

At block 1316, vLP 604 receives the AP event marker transmitted at block 1308. In response, vLP 604 blanks (i.e., ignores) sense inputs of vLP 604 during the atrial pace pulse at block 1318, and starts PAVB at block 1320. At block 1322, vLP 604 cancels any ongoing VVEI timer 612, and starts an AVEI timer 614 at block 1324. The AVEI timer 614 is initialized at a target AV interval (e.g., a target paced AV interval) which may also be adjusted based on the target rate information. In the embodiment illustrated in FIG. 13, blocks 1320, 1322, and 1324 occur in sequential order; however, in other embodiments, these blocks may occur in any order or may occur simultaneously.

Figure 14:
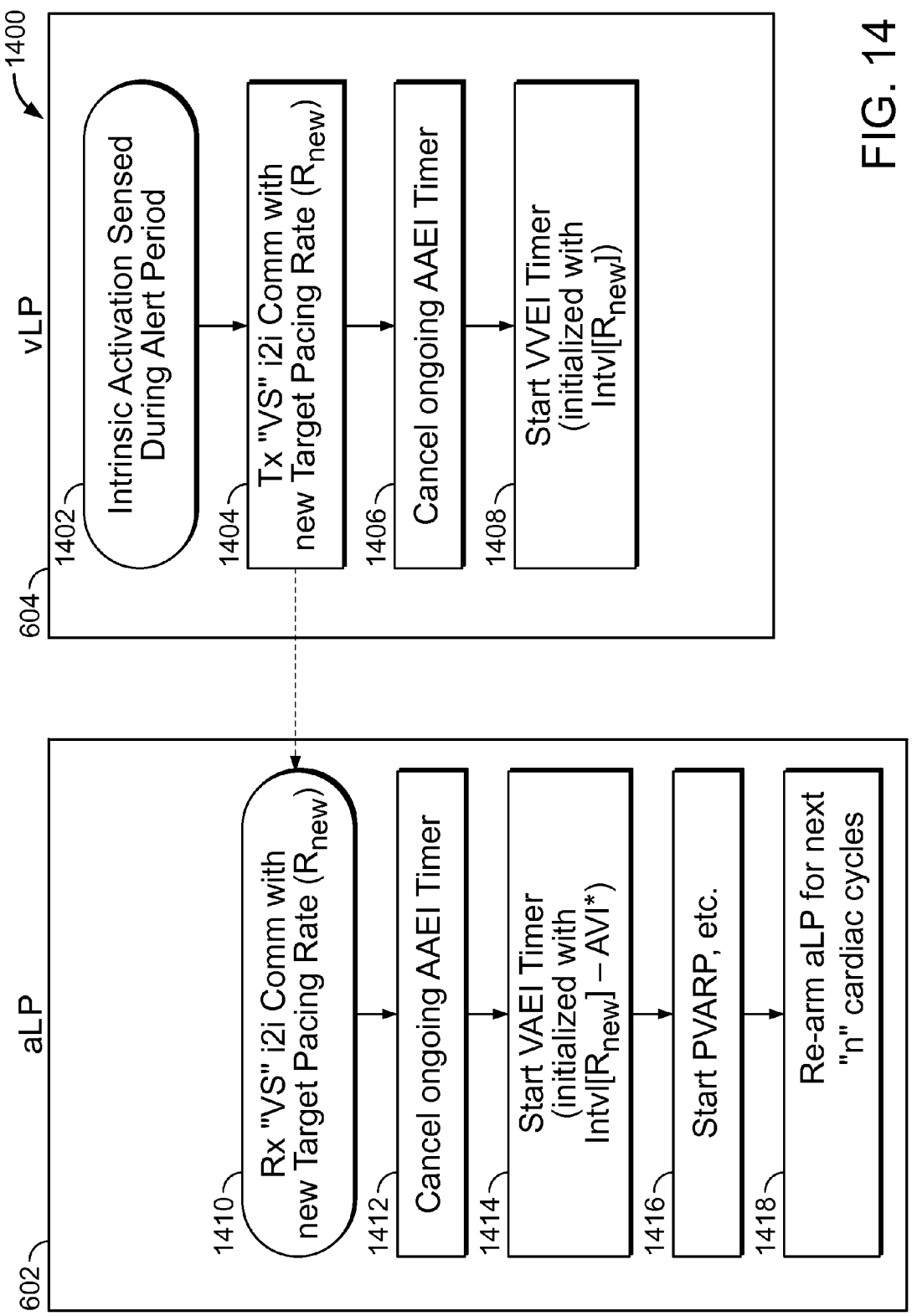
FIG. 14 is a flow chart illustrating operation of an aLP and a vLP during a ventricular sense event in accordance with one embodiment.

FIG. 14 is a flow chart 1400 illustrating operation of aLP 602 and vLP 604 upon a ventricular sense event. At block 1402, vLP 602 senses an intrinsic activation during an alert period. In response, vLP 602 transmits a VS event marker to aLP 604 at block 1404. Notably, the VS event marker may include rate information. Specifically, in this embodiment VS event marker includes a target pacing rate, $R_{new}$. The target pacing rate may be expressed as an absolute value or a relative value, as described above. In this embodiment, the target pacing rate is in units of inverse minutes ($min^{-1}$). vLP 604 also cancels any ongoing AVEI timer 614 at block 1406, and starts a VVEI timer 612 at block 1408. In this embodiment, VVEI timer 612 is initialized with $Intvl[R_{new}]$, wherein $Intvl[R_{new}]=60000/R_{new}$, and is expressed in ms.

At block 1410, aLP 602 receives the VS marker (possibly including the target pacing rate) transmitted at block 1404. In response, aLP 602 cancels any ongoing AAEI timer 610 at block 1412, and starts a VAEI timer 616 at block 1414. VAEI timer 616 is initialized as the difference between $Intvl[R_{new}]$ and AVI* (i.e., $Intvl[R_{new}]-AVI^*$). For an atrial based timing scheme, AVI* is a measured atrioventricular (AV) interval. For a ventricular based timing scheme, AVI* is a programmed AV interval (possibly adjusted, as appropriate, for rate-responsiveness).

At block 1416, PVARP and other local refractory timers as appropriate are initiated by aLP 602, and at block 1418, aLP 602 is re-armed for the next "n" atrial cardiac cycles (i.e., combination of intrinsic sensed events and pace requests). In this embodiment, n=2. Alternatively, n may be 1 or any other suitable integer (e.g., n=3, n=5, n=10, etc.).

Figure 15:
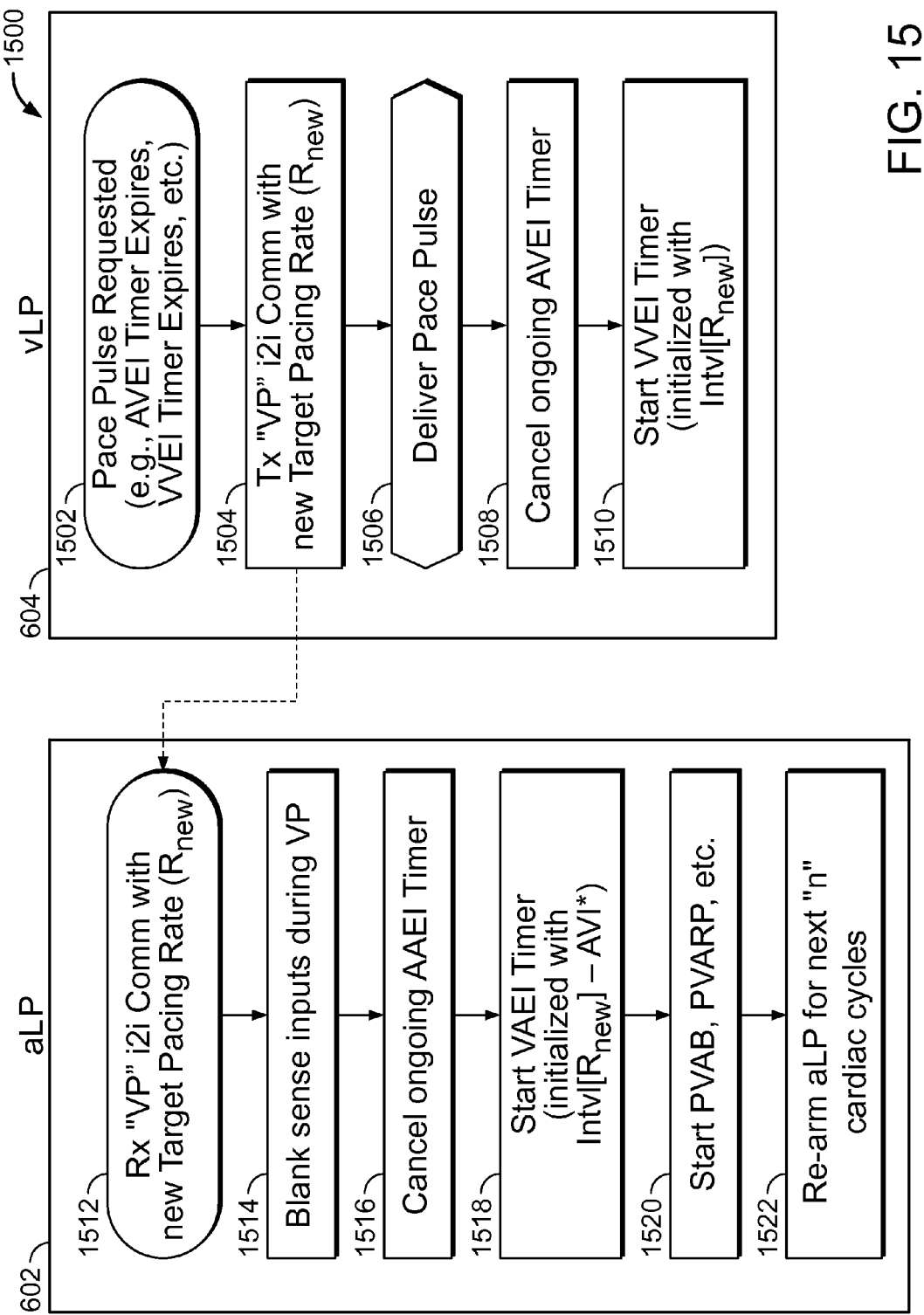
FIG. 15 is a flow chart illustrating operation of an aLP and a vLP during a ventricular pace event in accordance with one embodiment.

FIG. 15 is a flow chart 1500 illustrating operation of aLP 602 and vLP 604 upon a ventricular pace event. At block 1502, a ventricular pace pulse is requested (e.g., in response an AVEI timer 614 expiring, or VVEI timer 612 expiring, etc.). In response, vLP 604 transmits a VP event marker to aLP 602 at block 1504. Notably, the VP event marker may include rate information. Specifically, in this embodiment, VP event marker includes a target pacing rate, $R_{new}$. The target pacing rate may be expressed as an absolute value or a relative value, as described above. In this embodiment, the target pacing rate is in units of inverse minutes ($min^{-1}$). vLP 604 delivers a pace pulse at block 1506.

At block 1508, vLP 604 cancels any ongoing AVEI timer 614, and starts a VVEI timer 612 at block 1510. In this embodiment, VVEI timer 612 is initialized with $Intvl[R_{new}]$, wherein $Intvl[R_{new}]=60000/R_{new}$, and is expressed in ms.

At block 1512, aLP 602 receives the VP marker (possibly including the target pacing rate) transmitted at block 1504. In response, aLP 602 blanks (i.e., ignores) sense inputs during the ventricular pace pulse at block 1514, and aLP 602 cancels any ongoing AAEI timer 610 at block 1516. At block 1518, aLP 602 starts a VAEI timer 616. VAEI timer 616 is initialized as the difference between $Intvl[R_{new}]$ and AVI* (i.e., $Intvl[R_{new}]-AVI^*$). For an atrial based timing scheme, AVI* is a measured atrioventricular (AV) interval. For a ventricular based timing scheme, AVI* is a programmed AV interval (possibly adjusted, as appropriate, for rate-responsiveness).

At block 1520, aLP 602 starts, PVAB, PVARP, and other local refractory timers as appropriate. Further, at block 1522, aLP 602 is re-armed for the next "n" atrial cardiac cycles (i.e., combination of intrinsic sensed events and pace requests). In this embodiment, n=2. Alternatively, n may be 1 or any other suitable integer (e.g., n=3, n=5, n=10, etc.).

Another approach to providing variable rate-response atrial-based pacing is to incorporate a rate-response sensor and algorithm in the aLP device. Then it becomes unnecessary to communicate a changing rate from the vLP to the aLP. It may then, however, be necessary or desirable to communicate new target rate information from the aLP to the vLP.

In accordance with some embodiments, forward arming allows i2i marker transmissions to occur substantially concurrent with local pace or sense events. As such, forward arming avoids the risk of inducing premature ventricular or atrial excitations via marker transmissions. "Bridging" capability enables the aLP to preserve short-term functionality through one or more missed/corrupted V2A markers. In the face of any breakdown in i2i communications (prolonged or transient beyond bridgeable cycles), the system will inherently revert to safe ventricular-based pace/sense functionalities because the vLP device is running at least all of the algorithms necessary to maintain these ventricular-based pace/sense functionalities, and its pace/sense activities do not depend on i2i communication. Once i2i communications are restored, the system will inherently resume dual-chamber functionalities.

Balanced Operation

In accordance with embodiments herein, the ventricular and atrial LPs may be configured to operate in a substantially balanced manner in which dual chamber sensing and pacing functions/algorithms are divided between the atrial and ventricular LPs. Table 7 below illustrates examples of the functions that may be divided between the atrial and ventricular LPs.

TABLE 7

| Function | Implemented or Governed by |
| --- | --- |
| Rate-response (sensor-indicated rate) | aLP, for all atrial-only or dual-chamber modes<br>vLP, for all ventricular-only or "i2i safe" modes ("i2i safe" mode described below) |
| PVARP | aLP |
| AMS | aLP |
| PVC Response | aLP & vLP |
| PMT Response | aLP |
| Rate-responsive AV Delay [RRAVD] | vLP |
| Ventricular Intrinsic Preference [VIP] | vLP |
| Ventricular Safety Standby [VSS] | vLP |

As shown in Table 7, the rate responsive operation may be implemented or governed by the atrial LP when in an atrial only mode, and/or by the ventricular LP when in a ventricular only mode, a dual chamber mode, or when reversion to a safe (e.g., ventricular only) operating mode occurs during transient or prolonged loss of i2i communications. The atrial LP may also implement the functions and operations that wholly or in part manage one or more of the PVARP timer, automatic mode switching (AMS), premature ventricular contraction (PVC) response, pacemaker mediated tachycardia (PMT) response and the like. The ventricular LP may also implement the functions and operations that manage PVC responses, as well as managing the rate responsive AV delay, ventricular intrinsic preferences, ventricular safety standby and the like.

As explained herein, communication and synchronization between the aLP and vLP is implemented via conducted communication of event markers (per i2i communication protocol). The i2i communication markers may be emitted only substantially concurrent with a local pace or sense event. As such, there is no risk of emitting a marker during a vulnerable period, and thus no risk of inducing unintended excitations. The i2i communication event markers are optionally expanded with a code to indicate whether the transmitting device successfully received a valid i2i marker from the remote LP since the last transmission from the remote LP. For example, a simple example of this coding uses a binary indicator (e.g., 0/1, Ack/Nack, etc.). Optionally, more sophisticated coding schemes could alternatively be employed to include expanded information, e.g., number of consecutive missed markers, handshaking to provide insight into which marker(s) were missed, etc. These "acknowledgement codes" may be used by both LPs to diagnosis bidirectional and/or unidirectional breakdowns in i2i communication, so that the LP can take remedial actions as appropriate. One such remedial action (e.g., for transient losses of i2i communications) would be to "bridge" one or more missed/corrupted markers for n future cycles before reverting to an "i2i safe" operating mode. Another such remedial action (e.g., for more prolonged losses of i2i communications) would be to revert to an "i2i safe" mode so as to avoid possibilities of asynchronous pacing by aLP and vLP.

One example of an "i2i safe" mode is the transition from dual-chamber functionality to ventricular-only functionality (e.g., DDDR to VVIR). The LPs would exit from "i2i safe" mode and return to the programmed dual-chamber mode once bidirectional i2i communication has been reestablished. As another example of an alternative "i2i safe" mode, when the LPs experience unidirectional loss of V2A i2i communication (i.e., A2V i2i communication remains intact), the aLP and vLP may transition from DDDR to VDDR.

The following Tables 8 and 9 summarize one embodiment of the basic i2i markers and their associated behaviors when operating in a balanced mode.

TABLE 8

"A2V" Markers (i.e., from aLP to vLP)

| Marker | Description | Result in aLP/vLP |
| --- | --- | --- |
| AS | Notification of a sensed event in atrium | If 'i2i normal':<br>  aLP: Initiate AAEI timer based on target rate.<br>  vLP: Initiate AVEI timer.<br>If "i2i safe":<br>  vLP: Used only to indicate good A2V when attempting to reestablish 'i2i normal'. |
| AP | Notification of a paced event in atrium | If 'i2i normal':<br>  aLP: Initiate AAEI timer based on target rate.<br>  vLP: Initiate PAVB. |

TABLE 8-continued

"A2V" Markers (i.e., from aLP to vLP)

| Marker | Description | Result in aLP/vLP |
| --- | --- | --- |
| | |   vLP: Initiate AVEI timer.<br>If "i2i safe":<br>  vLP: Used only to indicate good A2V when attempting to reestablish 'i2i normal'. |
| AN | Notification of a 'null' event in atrium (a 'null' event [an event marker not associated with a pace or sense event] is used by the aLP while in "i2i safe" mode only during attempts to reestablish bidirectional i2i communication with vLP) | If 'i2i normal':<br>  Not used.<br>If "i2i safe":<br>  vLP: Used only to indicate good A2V when attempting to reestablish 'i2i normal' and no intrinsic atrial activity is present. |

TABLE 9

"V2A" Markers (i.e., from vLP to aLP)

| Marker | Description | Result in aLP/vLP |
| --- | --- | --- |
| VS | Notification of a sensed event in ventricle | If 'i2i normal':<br>  vLP: Initiate VVEI timer based on previous VV interval.<br>If "i2i safe":<br>  aLP: Initiate VAEI timer based on prev VV intvl - AVI<br>  vLP: Initiate VVEI timer based on target rate. |
| VP | Notification of a paced event in ventricle | If 'i2i normal':<br>  aLP: Initiate PVAB.<br>  vLP: Initiate VVEI timer based on previous VV interval.<br>If "i2i safe":<br>  aLP: Initiate VAEI timer based on prev VV intvl - AVI<br>  vLP: Initiate VVEI timer based on target rate. |

Special Messages

In accordance with some embodiments, message extensions (also referred to as secondary information) may be added to the event messages. For example, occasionally there may be a desire to exchange additional "more sophisticated" notifications and/or information between the atrial and ventricular LP (or IMDs in general) in addition to the above basic marker information. In one example, an encoded "message" may be embedded within or appended to the standard i2i message only when needed. In this example embodiment, one encoded message would be sent within any single i2i communication. In an alternative embodiment, multiple encoded messages can be sent within a single i2i communication, for example by "daisy-chaining" those messages onto the single i2i communication or by combining those messages into one compound message. Accordingly, these encoded messages can be prioritized as appropriate so that the most-critical message of all pending messages is sent first. Subsequent messages may then be sent in order of remaining priorities once those higher-priority messages are completed, cleared, or acknowledged (as appropriate for that associated message). Examples of possible messages include (not exhaustive; not prioritized) the following in Table 10.

TABLE 10

| Message | Description | Sent until . . . |
| --- | --- | --- |
| Magnet Applied | Sent when a magnet is detected (assumes Magnet Mode is ON) | Sent during each cycle that magnet is detected; cleared thereafter |
| AMS Entry | Sent when Auto Mode Switch [AMS] is initiated | Sent during each cycle until remote LP acknowledges receipt of notification |
| AMS Exit | Sent when Auto Mode Switch [AMS] is exited | Sent during each cycle until remote LP acknowledges receipt of notification |
| RRT Reached | Sent when either device reaches RRT | Sent during each cycle until remote LP acknowledges receipt of notification |
| PVC Detected | Sent if vLP detects PVC (per PVC definition) | Sent only with VS marker associated with the detected PVC itself |

A magnet externally-applied to a patient that has been implanted with a pulse generator (e.g., pacemaker, ICD, etc.) is a standard means to (a) immediately initiate non-inhibited fixed-rate pacing (e.g., DOO, VOO, or AOO mode, as appropriate), and/or (b) provide a quick means to assess the pulse generator's battery status (via a standardized pattern of induced pacing rates). With the use of two independent LPs operating in a dual-chamber mode, it is desirable that these LPs respond to an applied magnet in a consistent and synchronized manner (assuming that Magnet Mode functionality is available and selected). One means to accomplish this response synchronization is to send a special message from a first LP to a second LP indicating that a magnet has been (or is being) actively detected by the first LP. This special message could be sent with each i2i communication from the first LP to the second LP in which the magnet is detected by the first LP (and thus the absence of the special message would implicitly signify that the magnet is no longer detected). Alternatively, a special "sense magnet" message could be sent from the first LP to the second LP to indicate initial detection of the magnet by the first LP, and then a separate special message could be sent to indicate loss of detection of that magnet by the first LP. In this alternative approach, return messages from the second LP to the first LP that acknowledge receipt of each original special message would be a preferred additional option.

The LPs could be functionally configured such that both LPs (e.g., aLP and vLP) are sensitive and directly responsive to any applied magnet. In this "balanced magnet response" configuration, if either LP detects the magnet, the magnet-sensing LP transmits the special message to the other LP indicating that a magnet has been detected. Alternatively, the LPs could be functionally configured such that only a single LP (e.g., the vLP) is sensitive and directly responsive to an applied magnet. In this "master/slave magnet response" configuration, if (and only if) the magnet-sensitive LP (e.g. the vLP) detects the magnet, that LP transmits the special message to the other LP (e.g. the aLP) indicating that a magnet has been detected.

Upon detection of the applied magnet by the first LP and receipt of the associated special message by the second LP, the LPs would immediately and synchronously initiate the appropriate pre-defined or programmed Magnet Mode protocol. For example, the LPs would immediately transition from their programmed dual-chamber functional mode (e.g., DDDR) to the defined non-inhibited fixed-rate magnet mode (e.g., DOO or VOO). Furthermore, the pattern and/or rate of pacing output would conform to the defined magnet mode protocol (e.g., per AAMI PC88). The magnet mode settings would be maintained by both LPs until the magnet is no longer detected, at which point the LPs would synchronously revert to their normal mode and functionality.

Figure 16:
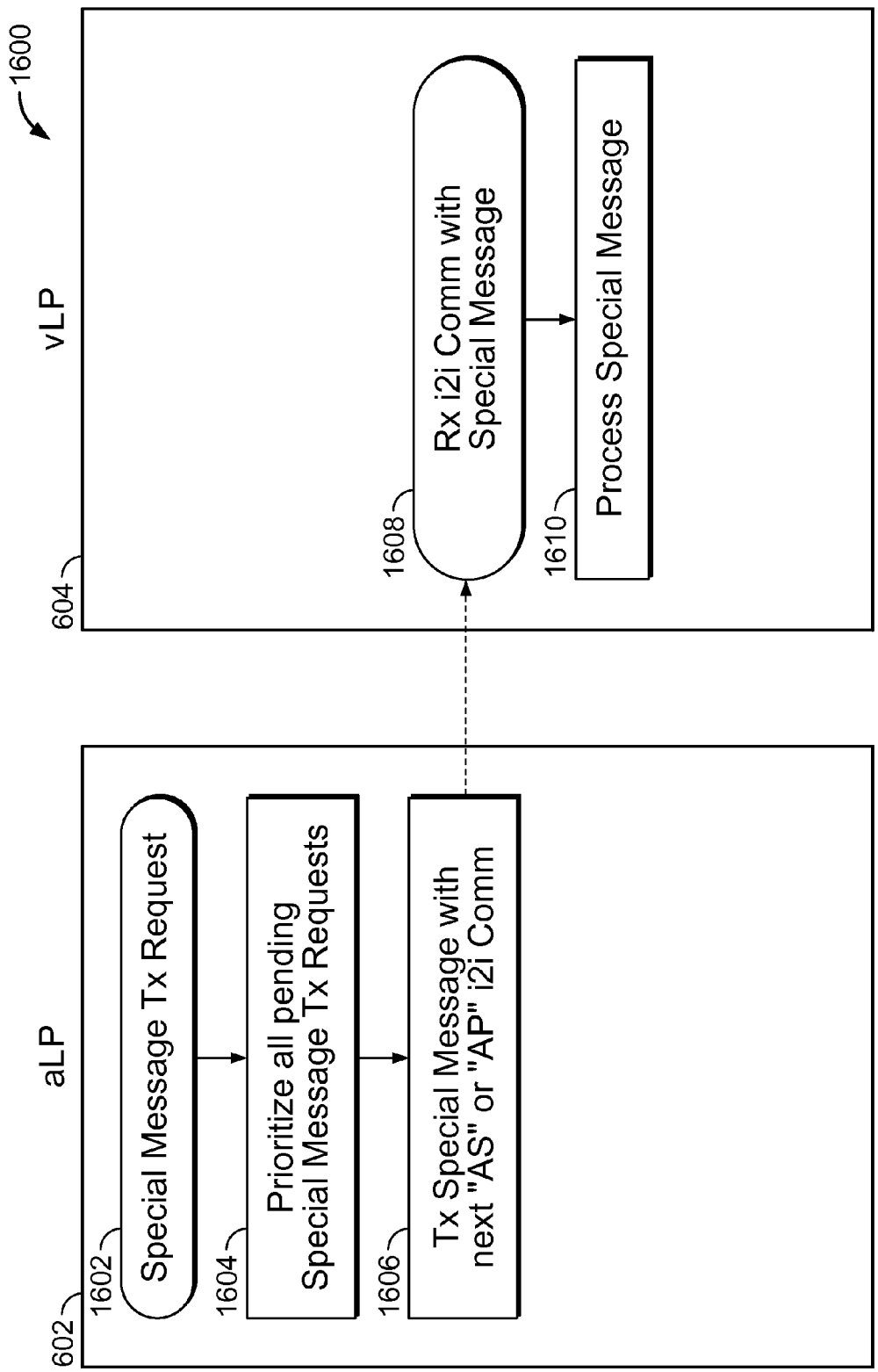
FIG. 16 is a flow chart of one embodiment of a method for transmitting a special message from an aLP to a vLP.

FIG. 16 is a flow chart of one embodiment of a method 1600 for transmitting a special message from aLP 602 to vLP 604. Those of skill in the art will appreciate that an equivalent method could be used to transmit a special message from vLP 604 to aLP 602.

At block 1602, a special message transmission request is initiated. The special message may be, for example, a message indicating that aLP 602 has detected activation of a magnet, as described above. At block 1604, in this embodiment, all pending special message transmission requests are prioritized, such that only the highest-priority special message in the special message queue will be transmitted before all other pending messages. In some embodiments, only a subset of pending messages will be transmitted. In other embodiments, all pending special messages are transmitted with each event marker transmission, and thus block 1604 need not be included in method 1600.

At block 1606, aLP 602 transmits the special message to vLP 604 with the next AS or AP event marker. At block 1608, vLP 604 receives the AS or AP event marker and the special message, and at block 1610, vLP 604 processes the special message accordingly.

Figure 17:
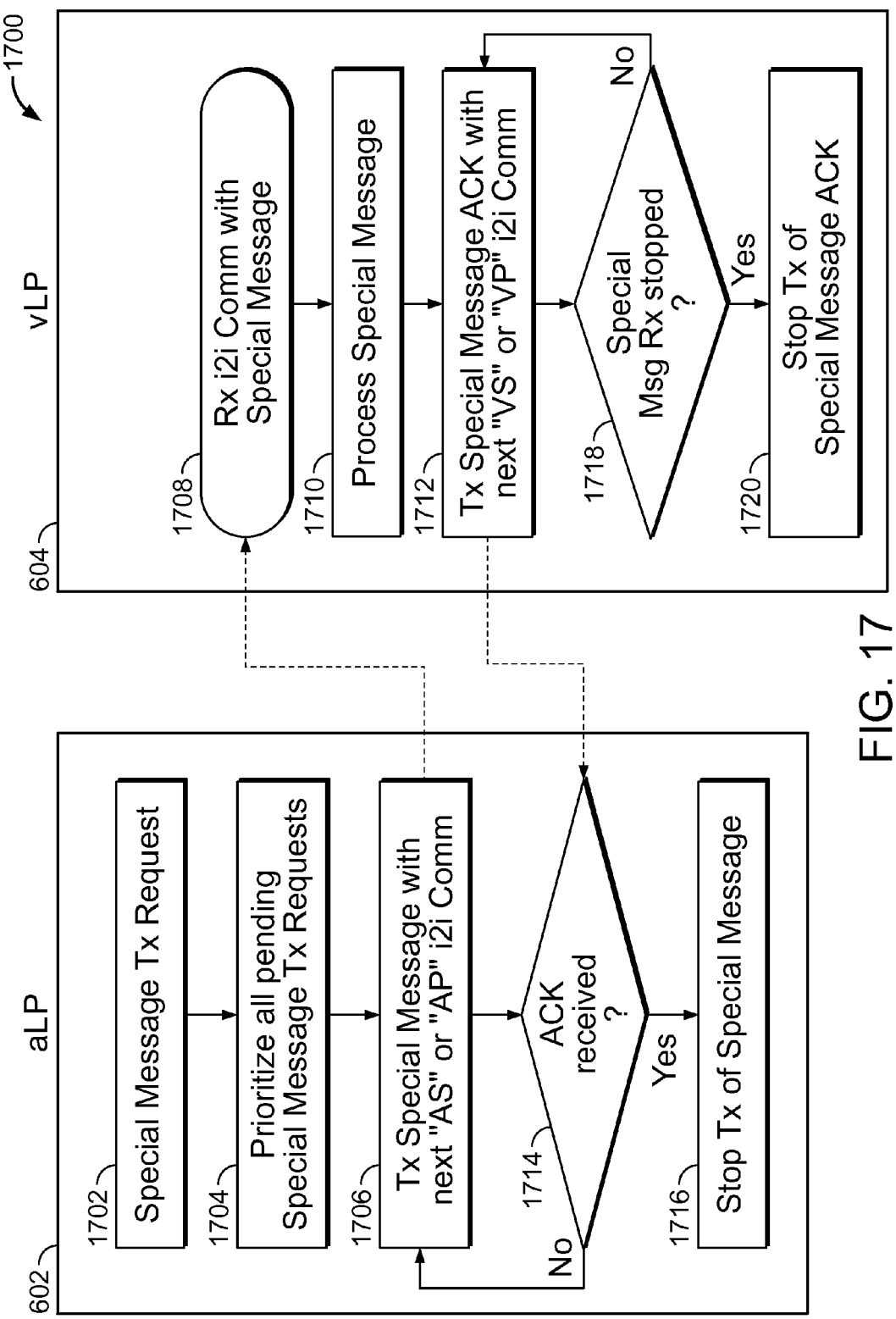
FIG. 17 is a flow chart of an alternative embodiment of a method for transmitting a special message from an aLP to a vLP.

FIG. 17 is a flow chart of one embodiment of a method 1700 for transmitting a special message from aLP 602 to vLP 604 where vLP 604 acknowledges receipt of the special message. Those of skill will appreciate that an equivalent method could be used to transmit a special message from vLP 604 to aLP 602.

At block 1702, a special message transmission request is initiated. At block 1704, in this embodiment, all pending special message transmission requests are prioritized, such that only the highest-priority special message in the special message queue will be transmitted before all other pending messages. In some embodiments, only a subset of pending messages will be transmitted. In other embodiments, all pending special messages are transmitted with each event marker transmission, and thus block 1704 need not be included in method 1700.

At block 1706, aLP 602 transmits the special message to vLP 604 with the next AS or AP event marker. At block 1708, vLP 604 receives the event marker and the special message, and at block 1710, vLP 604 initiates processing of the special message accordingly.

vLP 604 then transmits an acknowledgement to aLP 602 with the next VS or VP event marker at block 1712. At block 1714, aLP 602 determines whether the acknowledgement has been received. If no acknowledgment has been received, flow returns to block 1706, and aLP 602 transmits the special message again. If the acknowledgement is received, flow proceeds to block 1716, and aLP 602 stops transmitting the special message.

After vLP 604 transmits the acknowledgement at block 1712, vLP 604 determines whether the special message is still being received at block 1718. If the special message is still being received (i.e, receipt has not stopped), flow returns to block 1712, and vLP 604 again transmits the acknowledgement. If the special message receipt has stopped, flow proceeds to block 1720, and vLP 604 stops transmitting the acknowledgement.

Figure 18:
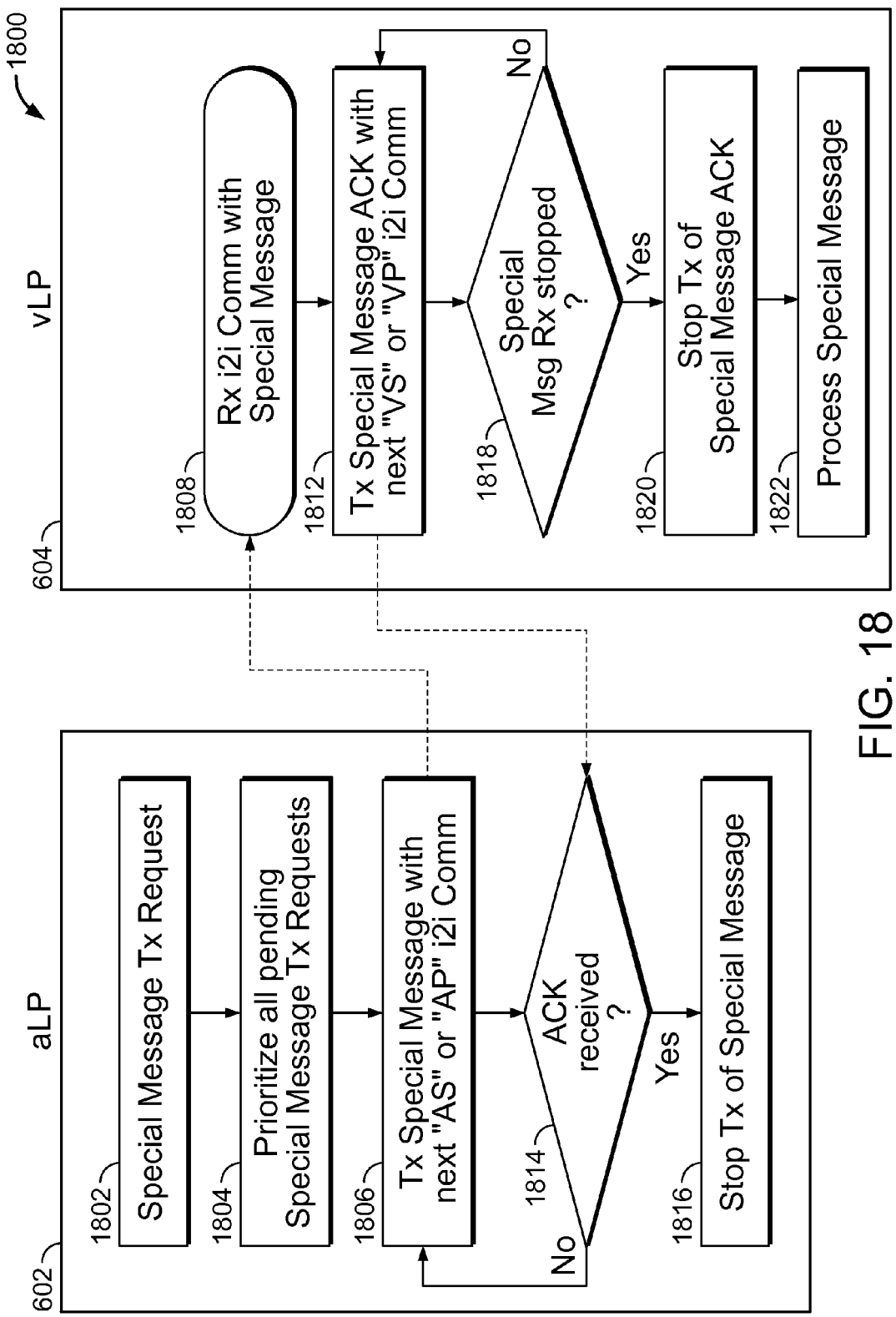
FIG. 18 is a flow chart of an alternative embodiment of a method for transmitting a special message from an aLP to a vLP.

FIG. 18 is a flow chart of an alternative embodiment of a method 1800 for transmitting a special message from aLP 602 to vLP 604 where vLP 604 acknowledges receipt of the special message. Those of skill will appreciate that an equivalent method could be used to transmit a special message from vLP 604 to aLP 602.

At block 1802, a special message transmission request is initiated. At block 1804, in this embodiment, all pending special message transmission requests are prioritized, such that special messages will be transmitted before other messages. In some embodiments, block 1804 is not included in method 1800.

At block 1806, aLP 602 transmits the special message to vLP 604 with the next AS or AP event marker. At block 1808, vLP 604 receives the event marker and the special message.

vLP 604 then transmits an acknowledgement to aLP 602 with the next VS or VP event marker at block 1812. At block 1814, aLP 602 determines whether the acknowledgement has been received. If no acknowledgment has been received, flow returns to block 1806, and aLP 602 transmits the special message again. If the acknowledgement is received, flow proceeds to block 1816, and aLP 602 stops transmitting the special message.

After vLP 604 transmits the acknowledgement at block 1812, vLP 604 determines whether the special message is still being received at block 1818. If the special message is still being received (i.e, receipt has not stopped), flow returns to block 1812, and vLP 604 again transmits the acknowledgement. If the special message receipt has stopped, flow proceeds to block 1820, and vLP 604 stops transmitting the acknowledgement. At block 1822, vLP 604 initiates processing of the special message.

Examples of types of special messages that may be transmitted using the methods described herein will now be described.

Auto Mode Switching (AMS) is a standard dual-chamber pacemaker feature that, upon detection of high atrial rates (e.g., during atrial fibrillation or flutter), provides automatic transition from an AV synchronous pacing mode to one without atrial tracking so as to avoid non-physiologically high ventricular rates that might otherwise result in adverse/symptomatic hemodynamic cardiac performance. Conversely, when the high atrial rate reverts to a more physiologic rate, AMS functionality will terminate and the pacemaker system will again transition back to an AV synchronous pacing mode. Furthermore, pacemaker systems may utilize these AMS entry and exit events as triggers to initiate additional actions, such as collecting diagnostic data, storing intracardiac electrograms, etc.

With the use of two independent LPs operating in a dual-chamber mode, it may be desirable that the LPs respond to AMS entry and exit events in a consistent and synchronized manner (assuming that AMS functionality is available and selected). One means to accomplish this response synchronization is to send a special message from a first LP to a second LP that indicates that the threshold for AMS entry or exit has been met. Since AMS entry/exit thresholds relate to atrial rates, a preferred implementation would be to have the aLP be directly responsible for determining AMS transitions, with the aLP then communicating that transition event to the vLP via a special message. Alternatively, the vLP could be responsible for determining AMS transitions via monitoring of the rate at which it receives atrial sense (AS) A2V i2i markers.

Since the underlying high atrial rate could persist for a relatively long and undetermined duration, an exemplary embodiment includes sending AMS special messages (e.g., an "AMS Entry" special message) from the first LP to the second LP upon reaching the AMS entry trigger, and then sending a separate 'AMS Exit' special message upon reaching the AMS exit trigger. In this approach, a return message would preferentially be sent from the second LP to the first LP to acknowledge receipt of the original AMS special message. Once the acknowledgment is confirmed, the first LP can discontinue sending the AMS special message to the second LP; likewise, once the transmission of the AMS special message stops, the second LP can discontinue sending the return message of acknowledgement to the first LP. Alternatively, the first LP can continuously transmit an AMS special message for as long as the AMS conditions continue to be met (and thus the absence of the AMS special message would implicitly signify that the conditions for maintaining AMS activation are no longer present).

In one embodiment, upon transmission and receipt of an 'AMS Entry' special message, the LPs would immediately and synchronously transition from their original operational mode (e.g., DDDR) to the predefined or programmed AMS non-tracking mode (e.g., DDIR). If additional actions have been predefined or programmed to be performed upon AMS entry, then those actions would also be initiated within the LPs as appropriate. Equivalently, upon transmission and receipt of an 'AMS Exit' special message (or equivalent, as described above), the LPs would immediately and synchronously transition from their AMS operational mode (e.g., DDIR) to their original operational mode (e.g., DDDR). If additional actions have been predefined or programmed to be performed upon AMS exit, then those actions would also be initiated within the LPs as appropriate.

It is likely that the separate and independent LPs will reach their individual recommended replacement times (RRT) at different points in their lifetimes (e.g., due to different initial battery capacities, different pacing output levels or burdens, etc.). However, it may be desirable or important for the dual-chamber system to react synchronously to the realization of RRT by either LP. For example, it may be desirable to turn off rate-responsiveness upon reaching RRT. As another example, it may be desirable to reduce the base rate upon reaching RRT. Modification of other features might also be considered.

One means to accomplish this RRT response synchronization is to send a special message from a first LP to a second LP that indicates that the RRT threshold has been reached in the first LP. Since reaching RRT is a singular transition event, it is envisioned that a preferred approach would be to send a 'RRT Reached' special message from the first LP to the second LP upon the former reaching its RRT threshold. In this preferred approach, a return message would preferentially be sent from the second LP to the first LP to acknowledge receipt of the original RRT special message. Once the acknowledgment is confirmed, the first LP can discontinue sending the RRT special message to the second LP; likewise, once the transmission of the RRT special message stops, the second LP can discontinue sending the return message of acknowledgement to the first LP.

In one embodiment, upon transmission and receipt of an "RRT Reached" special message, the LPs would immediately and synchronously transition from their original operational mode (e.g., DDDR) to the predefined or programmed post-RRT operational mode (e.g., DDD). If additional actions have been predefined or programmed to be performed upon RRT, then those actions would also be initiated within the LPs as appropriate.

Dual-chamber pacemakers typically utilize one or more approaches to respond to a detected premature ventricular contraction (PVC). With the use of two independent LPs operating in a dual-chamber mode, it may be desirable that these LPs respond to a detected PVC in a consistent and synchronized manner (assuming that one or more PVC response features are available and selected). One means to accomplish this response synchronization is to send a special message appended to the associated V2A i2i "VS" event marker that explicitly identifies this specific "VS" event as a PVC. Upon transmission and receipt of a 'PVC Detected' special message, the LPs would immediately and synchronously initiate their predefined or programmed PVC Response actions (e.g., PVARP extension, etc.).

Interleaved Conducted Communications

Figure 19:
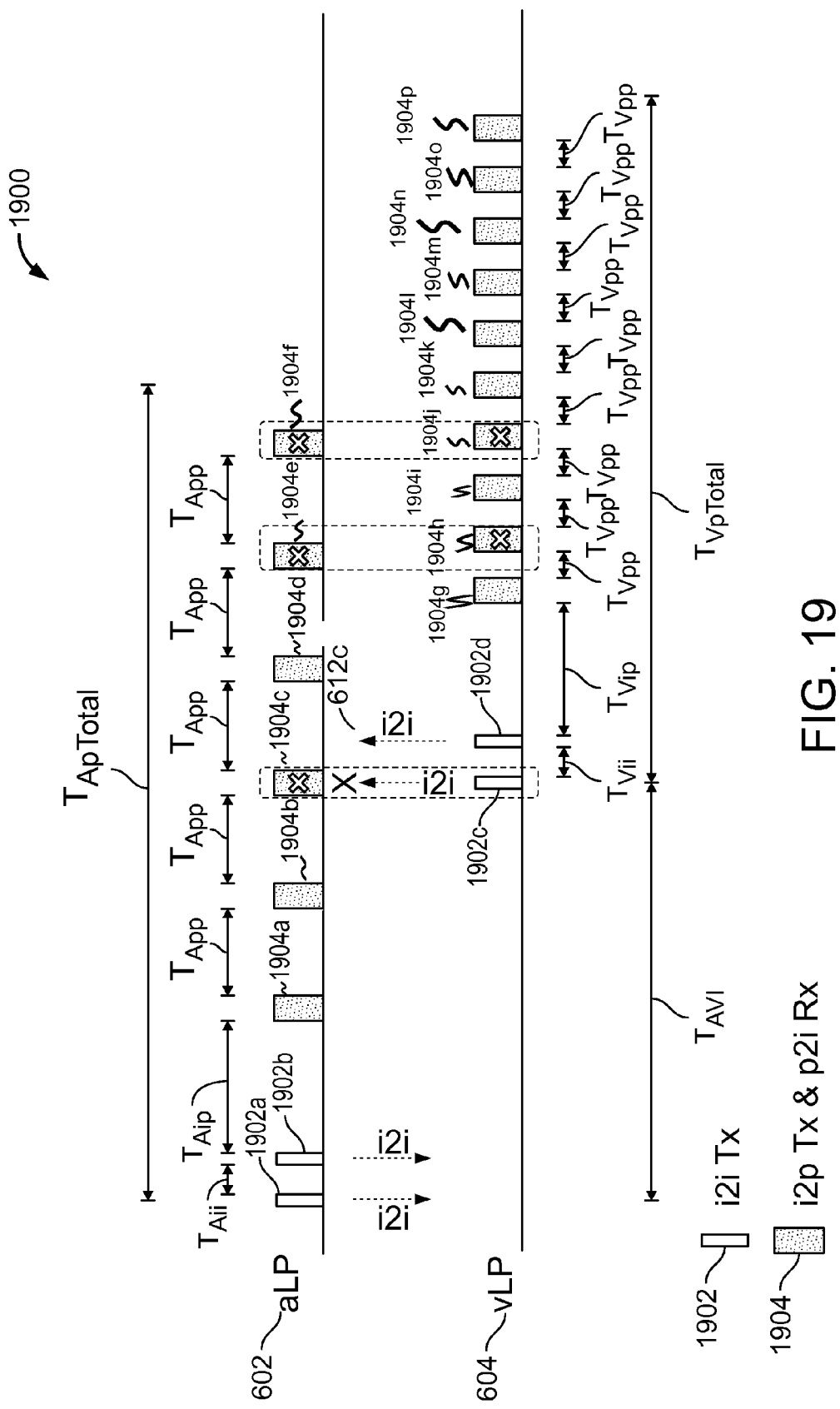
FIG. 19 is a timing diagram illustrating one embodiment of interleaved messaging between an aLP, a vLP, and a programmer.

FIG. 19 is a timing diagram 1900 illustrating one embodiment of interleaved messaging between aLP 602, vLP 604, and a programmer, such as programmer 109 (shown in FIG. 1) over a single cardiac cycle. Diagram 1900 shows i2i transmissions 1902 and i2p transmissions 1904 (i.e., transmissions from aLP 602 or vLP 604 to the programmer). However, if i2i transmissions 1902 and i2p transmissions 1904 are transmitted simultaneously, the communications may interfere with one another.

Accordingly, in this embodiment, i2i transmissions 1902 and i2p transmissions 1904 are repeated and sent at different intervals to facilitate ensuring that at least one instance of each message is successfully received. For example, as shown in FIG. 19, for a given event (e.g., an AS or AP event), during an atrial programmer total interval, $T_{ApTotal}$, aLP 602 transmits a first instance 1902a of an A2V i2i message and a second instance 1902b of the same i2i message at predetermined atrial implant-to-implant interval, $T_{Aii}$, following first instance 1902a. After an atrial wait interval, $T_{Aip}$, aLP 602 begins communicating with a programmer 109 via multiple i2p/p2i communication frames 1904a-f, with adjacent frames separated by atrial programmer frame-to-frame intervals, $T_{App}$.

Similarly, after an atrial ventricular interval, $T_{AVI}$, vLP 604 transmits a first instance 1902c of a V2A i2i message and a second instance 1902d of the same i2i message at a predetermined ventricular implant-to-implant interval, $T_{Vii}$. As shown in FIG. 19, first instance 1902c conflicts with an i2p transmission 1904a from aLP 602. However, second instance 1902d does not conflict with an i2p transmission 1904, and thus successfully reaches aLP 602. In this embodiment, interval $T_{Vii}$ is the same length as interval $T_{Aii}$. Alternatively, the intervals may have different lengths.

After a ventricular wait interval, $T_{Vip}$, vLP 604 begins communicating with a programmer 109 via multiple i2p/p2i communication frames 1904g-p, with adjacent frames separated by ventricular programmer frame-to-frame intervals, $T_{Vpp}$. In this embodiment, interval $T_{Vpp}$ is shorter than the interval $T_{App}$, such that aLP 601 transmits to the programmer less frequently than vLP 604. Alternatively, the intervals may have any suitable relative timing. vLP 604 communicates with aLP 602 and the programmer for a ventricular programmer total interval, $T_{VpTotal}$.

i2p transmissions/p2i receptions 1904 between aLP 602/programmer 109 and vLP 604/programmer 109 may collide, e.g., aLP 602 i2p/p2i 1904e is shown to conflict with vLP 604 i2p/p2i 1904h and aLP 602 i2p/p2i 1904f is shown to conflict with vLP 604 i2p/p2i 1904j. However, instance 1904 g, i, and k-p do not conflict with an i2p transmissions/p2i receptions 1904 between the other implant 602 and programmer 109, and thus successfully reach programmer 109. As shown in FIG. 19, transmitting each message multiple times, with different message sent at different intervals, facilitates ensuring that at least one instance of each message is successfully received.

Figure 20:
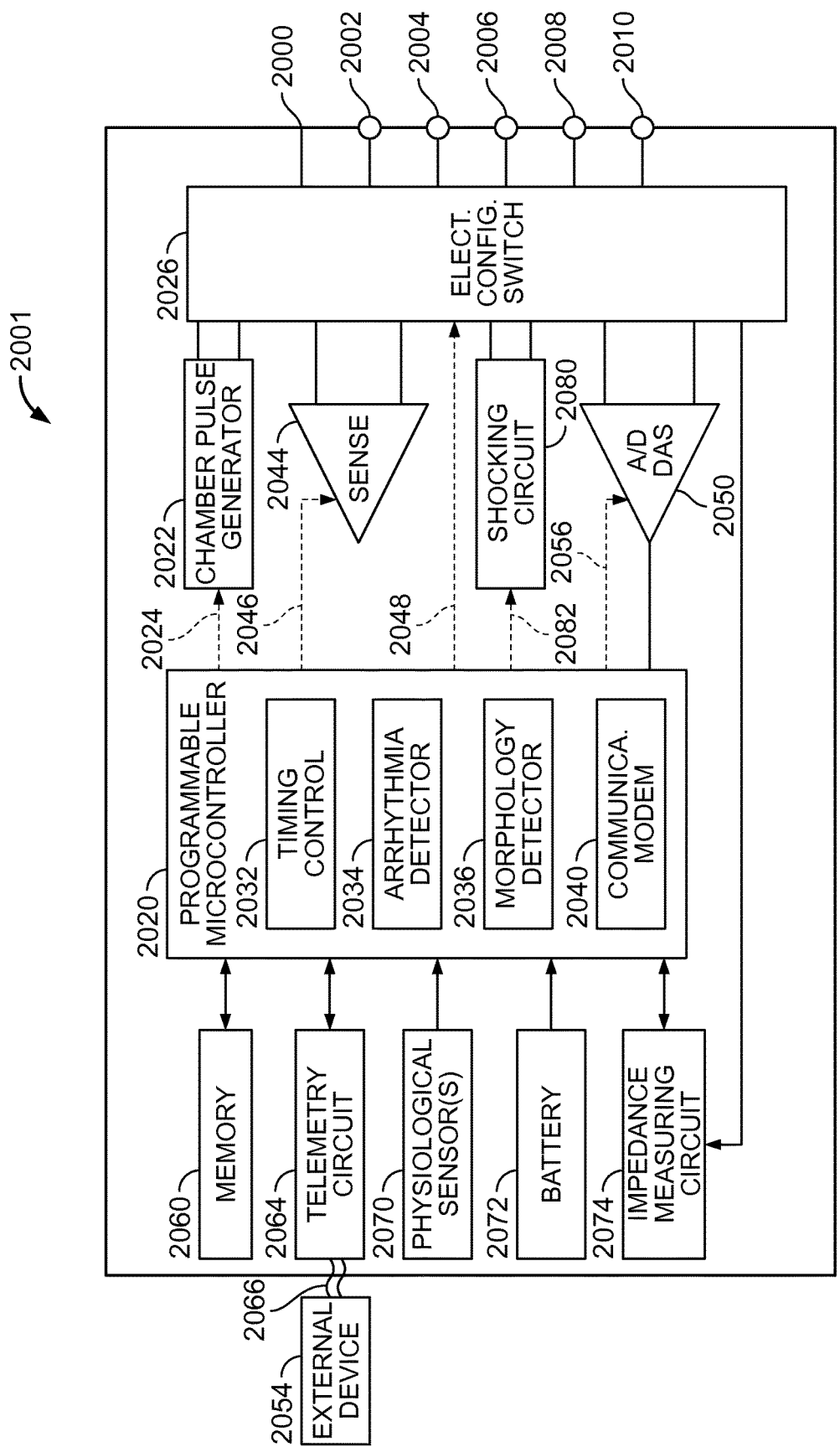
FIG. 20 is a block diagram of an LP that is implanted into the patient in accordance with embodiments herein.

FIG. 20 shows a block diagram of one embodiment of an LP 2001 that is implanted into the patient as part of the implantable cardiac system in accordance with embodiments herein. LP 2001 may be implemented as a full-function biventricular pacemaker, equipped with both atrial and ventricular sensing and pacing circuitry for four chamber sensing and stimulation therapy (including both pacing and shock treatment). Optionally, LP 2001 may provide full-function cardiac resynchronization therapy. Alternatively, LP 2001 may be implemented with a reduced set of functions and components. For instance, the IMD may be implemented without ventricular sensing and pacing.

LP 2001 has a housing 2000 to hold the electronic/computing components. Housing 2000 (which is often referred to as the "can", "case", "encasing", or "case electrode") may be programmably selected to act as the return electrode for certain stimulus modes. Housing 2000 may further include a connector (not shown) with a plurality of terminals 2002, 2004, 2006, 2008, and 2010. The terminals may be connected to electrodes that are located in various locations on housing 2000 or elsewhere within and about the heart. LP 2001 includes a programmable microcontroller 2020 that controls various operations of LP 2001, including cardiac monitoring and stimulation therapy. Microcontroller 2020 includes a microprocessor (or equivalent control circuitry), RAM and/or ROM memory, logic and timing circuitry, state machine circuitry, and I/O circuitry.

LP 2001 further includes a first pulse generator 2022 that generates stimulation pulses for delivery by one or more electrodes coupled thereto. Pulse generator 2022 is controlled by microcontroller 2020 via control signal 2024. Pulse generator 2022 may be coupled to the select electrode(s) via an electrode configuration switch 2026, which includes multiple switches for connecting the desired electrodes to the appropriate I/O circuits, thereby facilitating electrode programmability. Switch 2026 is controlled by a control signal 2028 from microcontroller 2020.

In the embodiment of FIG. 20, a single pulse generator 2022 is illustrated. Optionally, the IMD may include multiple pulse generators, similar to pulse generator 2022, where each pulse generator is coupled to one or more electrodes and controlled by microcontroller 2020 to deliver select stimulus pulse(s) to the corresponding one or more electrodes.

Microcontroller 2020 is illustrated as including timing control circuitry 2032 to control the timing of the stimulation pulses (e.g., pacing rate, atrio-ventricular (AV) delay, atrial interconduction (A-A) delay, or ventricular interconduction (V-V) delay, etc.). Timing control circuitry 2032 may also be used for the timing of refractory periods, blanking intervals, noise detection windows, evoked response windows, alert intervals, marker channel timing, and so on. Microcontroller 2020 also has an arrhythmia detector 2034 for detecting arrhythmia conditions and a morphology detector 2036. Although not shown, the microcontroller 2020 may further include other dedicated circuitry and/or firmware/software components that assist in monitoring various conditions of the patient's heart and managing pacing therapies.

LP 2001 is further equipped with a communication modem (modulator/demodulator) 2040 to enable wireless communication with the remote slave pacing unit. Modem 2040 may include one or more transmitters and two or more receivers as discussed herein in connection with FIG. 1B. In one implementation, modem 2040 may use low or high frequency modulation. As one example, modem 2040 may transmit i2i messages and other signals through conductive communication between a pair of electrodes. Modem 2040 may be implemented in hardware as part of microcontroller 2020, or as software/firmware instructions programmed into and executed by microcontroller 2020. Alternatively, modem 2040 may reside separately from the microcontroller as a standalone component.

LP 2001 includes a sensing circuit 2044 selectively coupled to one or more electrodes, that perform sensing operations, through switch 2026 to detect the presence of cardiac activity in the right chambers of the heart. Sensing circuit 2044 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 2026 determines the sensing polarity of the cardiac signal by selectively closing the appropriate switches. In this way, the clinician may program the sensing polarity independent of the stimulation polarity.

The output of sensing circuit 2044 is connected to microcontroller 2020 which, in turn, triggers or inhibits the pulse generator 2022 in response to the absence or presence of cardiac activity. Sensing circuit 2044 receives a control signal 2046 from microcontroller 2020 for purposes of controlling the gain, threshold, polarization charge removal circuitry (not shown), and the timing of any blocking circuitry (not shown) coupled to the inputs of the sensing circuitry.

In the embodiment of FIG. 20, a single sensing circuit 2044 is illustrated. Optionally, the IMD may include multiple sensing circuits, similar to sensing circuit 2044, where each sensing circuit is coupled to one or more electrodes and controlled by microcontroller 2020 to sense electrical activity detected at the corresponding one or more electrodes. Sensing circuit 2044 may operate in a unipolar sensing configuration or in a bipolar sensing configuration.

LP 2001 further includes an analog-to-digital (A/D) data acquisition system (DAS) 2050 coupled to one or more electrodes via switch 2026 to sample cardiac signals across any pair of desired electrodes. Data acquisition system 2050 is configured to acquire intracardiac electrogram signals, convert the raw analog data into digital data, and store the digital data for later processing and/or telemetric transmission to an external device 2054 (e.g., a programmer, local transceiver, or a diagnostic system analyzer). Data acquisition system 2050 is controlled by a control signal 2056 from the microcontroller 2020.

Microcontroller 2020 is coupled to a memory 2060 by a suitable data/address bus. The programmable operating parameters used by microcontroller 2020 are stored in memory 2060 and used to customize the operation of LP 2001 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 2001 may be non-invasively programmed into memory 2060 through a telemetry circuit 2064 in telemetric communication via communication link 2066 with external device 2054. Telemetry circuit 2064 allows intracardiac electrograms and status information relating to the operation of LP 2001 (as contained in microcontroller 2020 or memory 2060) to be sent to external device 2054 through communication link 2066.

LP 2001 can further include magnet detection circuitry (not shown), coupled to microcontroller 2020, to detect when a magnet is placed over the unit. A magnet may be used by a clinician to perform various test functions of LP 2001 and/or to signal microcontroller 2020 that external device 2054 is in place to receive or transmit data to microcontroller 2020 through telemetry circuits 2064.

LP 2001 can further include one or more physiological sensors 2070. Such sensors are commonly referred to as "rate-responsive" sensors because they are typically used to adjust pacing stimulation rates according to the exercise state of the patient. However, physiological sensor 2070 may further be used to detect changes in cardiac output, changes in the physiological condition of the heart, or diurnal changes in activity (e.g., detecting sleep and wake states). Signals generated by physiological sensors 2070 are passed to microcontroller 2020 for analysis. Microcontroller 2020 responds by adjusting the various pacing parameters (such as rate, AV Delay, V-V Delay, etc.) at which the atrial and ventricular pacing pulses are administered. While shown as being included within LP 2001, physiological sensor(s) 2070 may be external to LP 2001, yet still be implanted within or carried by the patient. Examples of physiologic sensors might include sensors that, for example, sense respiration rate, pH of blood, ventricular gradient, activity, position/posture, minute ventilation (MV), and so forth.

A battery 2072 provides operating power to all of the components in LP 2001. Battery 2072 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 2072 also desirably has a predictable discharge characteristic so that elective replacement time can be detected. As one example, LP 2001 employs lithium/silver vanadium oxide batteries.

LP 2001 further includes an impedance measuring circuit 2074, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 2074 is coupled to switch 2026 so that any desired electrode may be used. In this embodiment LP 2001 further includes a shocking circuit 2080 coupled to microcontroller 2020 by a data/address bus 2082.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A cardiac pacing system comprising:
a first implantable medical device (IMD) configured to transmit a first event message during or preceding a first cardiac cycle; and
a second IMD configured to receive the first event message, wherein receipt of the first event message configures the second IMD to generate pacing pulses for only a predetermined number ("n") of consecutive cardiac cycles, wherein n is an integer equal to or greater than 2, wherein the second IMD comprises a first escape interval timer and a second escape interval timer, and wherein receipt of the first event message:
configures the second IMD to initiate the first escape interval timer to generate a first pacing pulse, and
configures the second IMD to initiate the second escape interval timer for only a predetermined number of one or more subsequent consecutive cardiac cycles to generate one or more subsequent pacing pulses for the one or more subsequent consecutive cardiac cycles, wherein the second IMD is configured to initiate the second escape interval timer so as to configure the second IMD to generate a subsequent pacing pulse during only m immediately subsequent cardiac cycles, where m is an integer between one and ten.

2. The cardiac pacing system of claim 1, wherein the second IMD is further configured to sense one or more intrinsic cardiac events, and wherein receipt of the first event message configures the second IMD to initiate the second escape interval timer upon either:
generation of one or more subsequent pacing pulses by the second IMD, or sensing one or more intrinsic cardiac events by the second IMD during the one or more subsequent consecutive cardiac cycles.

3. The cardiac pacing system of claim 1, wherein the first IMD is configured to generate a pacing pulse and sense an intrinsic cardiac event, and wherein the first IMD is configured to transmit the first event message substantially concurrent with either:
generation of a pacing pulse using the first IMD, or
sensing the intrinsic cardiac event using the first IMD.

4. The cardiac pacing system of claim 1, wherein:
the first IMD is a leadless cardiac pacemaker configured to be implanted within a ventricle of a human heart (ventricular LP) to generate pacing pulses at a target pacing rate of the cardiac pacing system,
the second IMD is a leadless cardiac pacemaker configured to be implanted within an atrium of the human heart (atrial LP) to generate pacing pulses at the target pacing rate of the cardiac pacing system,
the cardiac pacing system is operable to change between a ventricular only operating mode, an atrial only operating mode, and a dual chamber operating mode,
only the atrial LP is configured to change the target pacing rate of the cardiac pacing system when the cardiac pacing system is in an atrial only operating mode, and
only the ventricular LP is configured to change the target pacing rate of the cardiac pacing system when the cardiac pacing system is in a ventricular only operating mode or a dual chamber operating mode.

5. The cardiac pacing system of claim 1, wherein:
first IMD is a leadless cardiac pacemaker configured to be implanted within a ventricle of a human heart (ventricular LP),
the second IMD is a leadless cardiac pacemaker configured to be implanted within an atrium of the human heart (atrial LP),
the ventricular LP is configured to implement all rate responsive operations of the cardiac pacing system except functions and operations that wholly or in part manage one or more of the PVARP timer, automatic mode switching (AMS), premature ventricular contraction (PVC) response, pacemaker mediated tachycardia (PMT) response, and
the atrial LP is configured to implement the functions and operations of the cardiac pacing system that wholly or in part manage one or more of the PVARP timer, automatic mode switching (AMS), premature ventricular contraction (PVC) response, pacemaker mediated tachycardia (PMT) response.

6. The cardiac pacing system of claim 1, wherein:
the first IMD is a leadless cardiac pacemaker configured to be implanted within a ventricle of a human heart (ventricular LP), the second IMD is a leadless cardiac pacemaker configured to be implanted within an atrium of the human heart (atrial LP), the first escape interval timer is a ventricular-to-atrial escape interval (VAEI) timer, and the second escape interval timer is an atrial-to-atrial escape interval (AAEI) timer.

7. The cardiac pacing system of claim 1, wherein:

the first IMD is further configured to deliver pacing pulses, the second IMD is further configured to transmit event messages, and at least one of the first or the second IMDs are configured to transmit event messages immediately preceding delivering pacing pulses in order to prepare the IMD receiving event messages for delivery of pacing pulses.

8. The cardiac pacing system of claim 1, further comprising an external device, and wherein the first IMD is further configured to:

repeatedly send the first event message to the second IMD at a first interval; and send a transmission to the external device ("i2p transmission") at a second interval, wherein the second interval is different from the first interval.

9. A cardiac pacing system comprising:

a first implantable medical device (IMD) configured to transmit a first event message during or preceding a first cardiac cycle; and a second IMD configured to receive the first event message, wherein receipt of the first event message configures the second IMD to generate pacing pulses for only a predetermined number ("n") of consecutive cardiac cycles, wherein n is an integer equal to or greater than 2, wherein the second IMD is configured to inhibit generation of a pacing pulse when the second IMD fails to receive the first event message within n cardiac cycles immediately preceding the first cardiac cycle.

10. The cardiac pacing system of claim 9, wherein the first event message further comprises rate information, and wherein the rate information is at least one of: a target pacing rate, a target pacing interval, or a change in target pacing rate.

11. A cardiac pacing system comprising:

a first implantable medical device (IMD) configured to transmit a first event message during or preceding a first cardiac cycle; and a second IMD configured to receive the first event message, wherein receipt of the first event message configures the second IMD to generate pacing pulses for only a predetermined number ("n") of consecutive cardiac cycles, wherein n is an integer equal to or greater than 2, wherein the second IMD comprises a first escape interval timer and a second escape interval timer, and wherein receipt of the first event message:

configures the second IMD to initiate the first escape interval timer to generate a first pacing pulse, and configures the second IMD to initiate the second escape interval timer for only a predetermined number of one or more subsequent consecutive cardiac cycles to generate one or more subsequent pacing pulses for the one or more subsequent consecutive cardiac cycles, wherein:

the first IMD is further configured to transmit a second event message during a cardiac cycle subsequent to the first cardiac cycle, the second IMD is further configured to receive the second event message, receipt of the second event message cancels the second escape interval timer and reinitiates the first escape interval timer of the second IMD, and the second IMD is further configured to generate a pacing pulse for a second cardiac cycle on expiration of the first escape interval timer.

12. A cardiac pacing system comprising:

a first implantable medical device (IMD) configured to transmit a first event message during or preceding a first cardiac cycle; and a second IMD configured to receive the first event message, wherein receipt of the first event message configures the second IMD to generate pacing pulses for only a predetermined number ("n") of consecutive cardiac cycles, wherein n is an integer equal to or greater than 2, wherein the second IMD comprises a first escape interval timer and a second escape interval timer, and wherein receipt of the first event message:

configures the second IMD to initiate the first escape interval timer to generate a first pacing pulse, and configures the second IMD to initiate the second escape interval timer for only a predetermined number of one or more subsequent consecutive cardiac cycles to generate one or more subsequent pacing pulses for the one or more subsequent consecutive cardiac cycles, wherein the first event message further comprises rate information, and wherein the second IMD is configured to set a duration of at least the first escape interval timer based on the rate information.

13. A method for providing communications between a first implantable medical device (IMD) and a second IMD, the method comprising:

transmitting a first event message during or preceding a first cardiac cycle from the first IMD;

receiving the first event message at the second IMD;

in response to receiving the first event message:

arming the second IMD to generate a first pacing pulse, and arming the second IMD to generate one or more subsequent pacing pulses for only a predetermined number of subsequent consecutive cardiac cycles, wherein:

arming the second IMD to generate the first pacing pulse comprises initiating a first escape interval timer, and arming the second IMD to generate the one or more subsequent pacing pulses for only the predetermined number of subsequent consecutive cardiac cycles comprises initiating a second escape interval timer; and canceling the second timer of the second IMD when a second event message from the first IMD to the second IMD is received.

14. The method of claim 13, wherein transmitting an event message comprises transmitting an event message that includes rate information, and wherein initiating a first timer comprises initiating a first timer having a first predetermined duration that is calculated based on the rate information.

15. A method for providing communications between a first implantable medical device (IMD) and a second IMD, the method comprising:

transmitting a first event message preceding a first cardiac cycle from the first IMD;

receiving the first event message at the second IMD;

in response to receiving the first event message:
arming the second IMD to generate a first pacing pulse, and
arming the second IMD to generate one or more subsequent pacing pulses for only a predetermined number of subsequent consecutive cardiac cycles;
generating a second pacing pulse using the first IMD; and
blanking the sense input of the second IMD after transmitting the first event message from the first IMD and immediately prior to generating the second pacing pulse using the first IMD.

16. A system for applying cardiac stimulation to a patient, the system comprising:
a first leadless pacemaker (LP) implanted in a first chamber of a heart of the patient, the first LP configured to:
transmit an event message during or preceding a first cardiac cycle, and deliver pacing pulses; and
a second LP implanted in either the first chamber of the heart or a second chamber of the heart of the patient, wherein:
the second LP is configured to: receive the first event message, wherein receipt of the first event message configures the second LP to generate pacing pulses for only a predetermined number ("n") of consecutive cardiac cycles, wherein n is an integer equal to or greater than 2, wherein the first LP is configured to transmit event messages immediately preceding delivering pacing pulses in order to prepare the second LP for delivery of pacing pulses.

* * * * *